United States Patent
Distelhorst et al.

(10) Patent No.: US 9,657,073 B2
(45) Date of Patent: May 23, 2017

(54) INHIBITORS OF BCL-2

(75) Inventors: Clark Distelhorst, Shaker Heights, OH (US); Yiping Rong, Baoshan (CN)

(73) Assignee: Case Western Reserve University, Cleveland, OH (US)

( * ) Notice: Subject to any disclaimer, the term of this patent is extended or adjusted under 35 U.S.C. 154(b) by 108 days.

(21) Appl. No.: 13/819,980

(22) PCT Filed: Sep. 1, 2011

(86) PCT No.: PCT/US2011/050183
§ 371 (c)(1),
(2), (4) Date: Apr. 26, 2013

(87) PCT Pub. No.: WO2012/031103
PCT Pub. Date: Mar. 8, 2012

(65) Prior Publication Data
US 2013/0217633 A1    Aug. 22, 2013

Related U.S. Application Data

(60) Provisional application No. 61/379,167, filed on Sep. 1, 2010.

(51) Int. Cl.
| | | |
|---|---|---|
| *A61K 38/00* | (2006.01) | |
| *A61K 38/16* | (2006.01) | |
| *A61K 38/10* | (2006.01) | |
| *C07K 14/47* | (2006.01) | |
| *C07K 14/705* | (2006.01) | |
| *A61K 38/17* | (2006.01) | |
| *A61K 45/06* | (2006.01) | |

(52) U.S. Cl.
CPC .......... *C07K 14/4703* (2013.01); *A61K 38/17* (2013.01); *A61K 45/06* (2013.01); *C07K 14/4747* (2013.01); *C07K 14/705* (2013.01); *A61K 38/00* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1
8,445,441 B2 * 5/2013 Distelhorst et al. ......... 514/18.9

2005/0244846 A1    11/2005 Johnson
2008/0261899 A1    10/2008 Cho et al.
2009/0048168 A1     2/2009 Distelhorst et al.

OTHER PUBLICATIONS

Blondel et al. Sequence and functional characterization of a third inositol trisphosphate receptor subtype, IP3R-3, expressed in pancreatic islets, kidney, gastrointestinal tract, and other tissues. Journal of Biological Chemistry. 1993; 268(15): 11356-63.*
Bowie et al. Deciphering the Message in Protein Sequences: Tolerance to Amino Acid Substitutions. Science, 247:1306-1310, 1990.*
Whisstock et al. Prediction of proteinfunction fromprotein sequence and structure. Quarterly Reviews in Biophysics. 36(3):307-340, 2007.*
Lazar et al. Transforming Growth Factor alpha: Mutation of Aspartic Acid 47 and Leucine 48 Results in Different Biological Activities. Molecular and Cellular Biology. 1988; 8(3): 1247-1252.*
Dewson et al. Bcl-2 family-regulated apoptosis in health and disease. Cell Health and Cytoskeleton. 2010; 2: 9-22.*
Rong et al. Targeting Bcl-2-1P3 Receptor Interaction to Reverse Bcl-2's Inhibition of Apoptotic Calcium Signals. Molecular Cell. 2008; 31:255-265.*
Kirkin et al. The role of Bcl-2 family members in tumorigenesis. Biochimica et Biophysica Acta. 2004; 1644:229-249.*
Heppner et al. Tumor heterogeneity biological implications and therapeutic consequences. Cancer Metastasis Review 2:5-23; 1983.*
Jain RK. Barriers to drug delivery in solid tumors. Scientific American, Jul. 1994, 58-65.*
Rong, Y.P., et al., "Targeting BCL-2 based on the interaction of its BH4 domain with the inositol 1,4,5-trisphosphate receptor", Biochem. Biophys. Acta, Jun. 2009, vol. 1793, No. 6, pp. 971-978.
Eckenrode, E.F., et al., "Apoptosis protection by Mcl-1 and Bcl-2 modulation of inositol 1,4,5-triphosphate receptor-dependent Ca2+ Signaling", J. Biol. Chem. Epub Feb. 26, 2010, vol. 285, No. 18, pp. 13678-13684.

* cited by examiner

*Primary Examiner* — Vanessa L Ford
*Assistant Examiner* — Sandra Dillahunt
(74) *Attorney, Agent, or Firm* — Tarolli, Sundheim, Covell & Tummino LLP

(57) ABSTRACT

A protease resistant polypeptide includes an amino acid sequence that has a sequence identity at least 80% homologous to about 10 to 80 consecutive amino acids of SEQ ID NO:1.

11 Claims, 14 Drawing Sheets

Figs. 4A-B

A
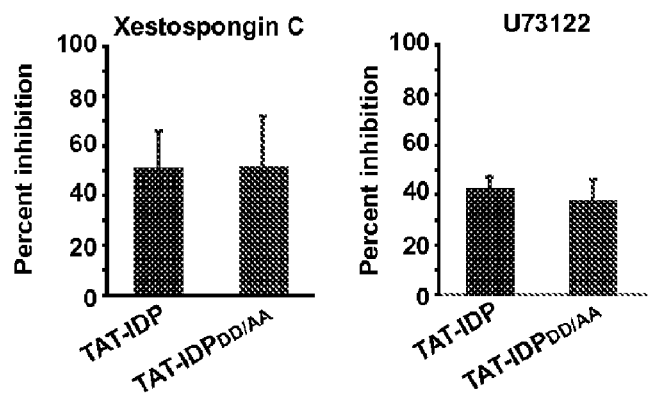
B
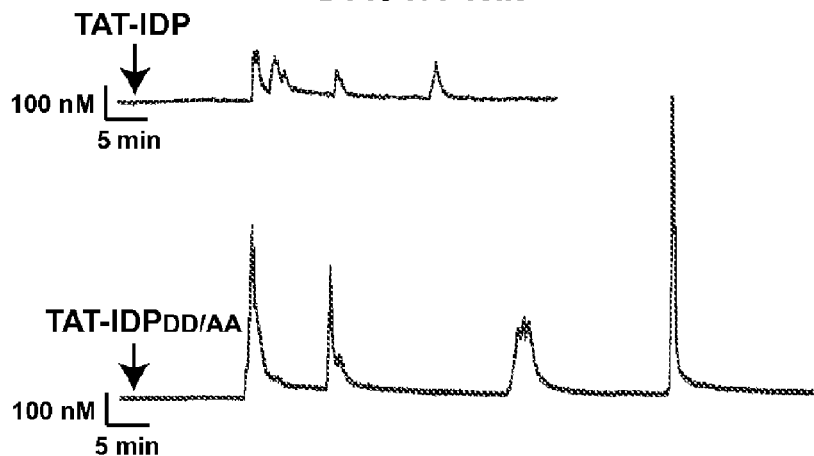
C
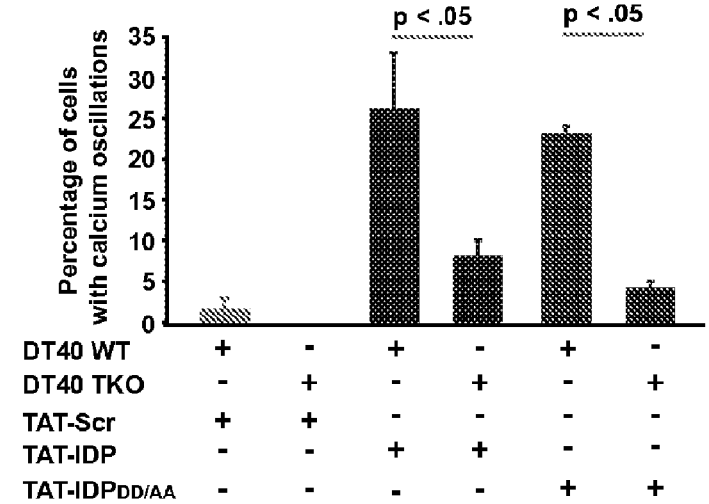
Figs. 8A-C

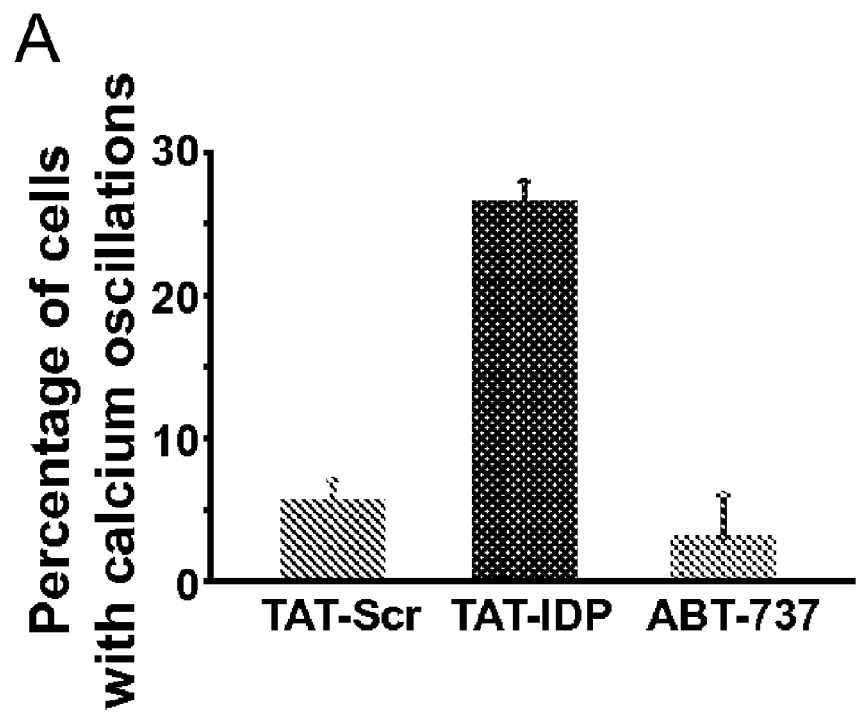
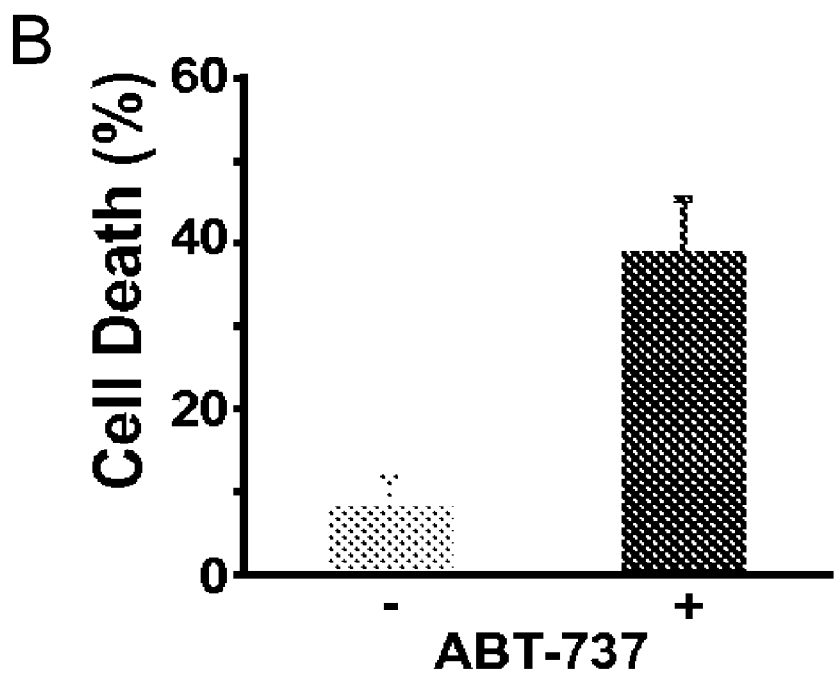
Figs. 11A-B

SEQUENCE LISTING

<160> NUMBER OF SEQ ID NOS: 12

<210> SEQ ID NO 1
<211> LENGTH: 80
<212> TYPE: PRT
<213> ORGANISM: Homo sapiens

<400> SEQUENCE: 1

Glu Arg Asp Arg Met Asp Glu Asn Ser Pro Leu Met Tyr His Ile His
1               5                   10                  15

Leu Val Glu Leu Leu Ala Val Cys Thr Glu Gly Lys Asn Val Tyr Thr
            20                  25                  30

Glu Ile Lys Cys Asn Ser Leu Leu Pro Leu Asp Asp Ile Val Arg Val
        35                  40                  45

Val Thr His Glu Asp Cys Ile Pro Glu Val Lys Ile Ala Tyr Ile Asn
    50                  55                  60

Phe Leu Asn His Cys Tyr Val Asp Thr Glu Val Glu Met Lys Glu Ile
65                  70                  75                  80

<210> SEQ ID NO 2
<211> LENGTH: 80
<212> TYPE: PRT
<213> ORGANISM: Homo sapiens

<400> SEQUENCE: 2

Glu Arg Ala Arg Met Ala Glu Asn Ser Pro Leu Met Tyr His Ile His
1               5                   10                  15

Leu Val Glu Leu Leu Ala Val Cys Thr Glu Gly Lys Asn Val Tyr Thr
            20                  25                  30

Glu Ile Lys Cys Asn Ser Leu Leu Pro Leu Ala Ala Ile Val Arg Val
        35                  40                  45

Val Thr His Glu Asp Cys Ile Pro Glu Val Lys Ile Ala Tyr Ile Asn
    50                  55                  60

Phe Leu Asn His Cys Tyr Val Ala Thr Glu Val Glu Met Lys Glu Ile
65                  70                  75                  80

<210> SEQ ID NO 3
<211> LENGTH: 80
<212> TYPE: PRT
<213> ORGANISM: Homo sapiens

<400> SEQUENCE: 3

Glu Arg Asp Arg Met Asp Glu Asn Ser Pro Leu Met Tyr His Ile His
1               5                   10                  15

Leu Val Glu Leu Leu Ala Val Cys Thr Glu Gly Lys Asn Val Tyr Thr
            20                  25                  30

Glu Ile Lys Cys Asn Ser Leu Leu Pro Leu Ala Ala Ile Val Arg Val
        35                  40                  45

Val Thr His Glu Asp Cys Ile Pro Glu Val Lys Ile Ala Tyr Ile Asn
    50                  55                  60

Phe Leu Asn His Cys Tyr Val Asp Thr Glu Val Glu Met Lys Glu Ile
65                  70                  75                  80

<210> SEQ ID NO 4
<211> LENGTH: 80
<212> TYPE: PRT
<213> ORGANISM: Homo sapiens

<400> SEQUENCE: 4

Glu Arg Glu Arg Met Glu Glu Asn Ser Pro Leu Met Tyr His Ile His
1               5                   10                  15

Leu Val Glu Leu Leu Ala Val Cys Thr Glu Gly Lys Asn Val Tyr Thr
            20                  25                  30

Glu Ile Lys Cys Asn Ser Leu Leu Pro Leu Glu Glu Ile Val Arg Val
        35                  40                  45

Val Thr His Glu Asp Cys Ile Pro Glu Val Lys Ile Ala Tyr Ile Asn
    50                  55                  60

Phe Leu Asn His Cys Tyr Val Glu Thr Glu Val Glu Met Lys Glu Ile
65                  70                  75                  80

<210> SEQ ID NO 5
<211> LENGTH: 80
<212> TYPE: PRT
<213> ORGANISM: Homo sapiens

<400> SEQUENCE: 5

Glu Arg Asp Arg Met Asp Glu Asn Ser Pro Leu Met Tyr His Ile His
1               5                   10                  15

Leu Val Glu Leu Leu Ala Val Cys Thr Glu Gly Lys Asn Val Tyr Thr
            20                  25                  30

Glu Ile Lys Cys Asn Ser Leu Leu Pro Leu Glu Glu Ile Val Arg Val
        35                  40                  45

Val Thr His Glu Asp Cys Ile Pro Glu Val Lys Ile Ala Tyr Ile Asn
    50                  55                  60

Phe Leu Asn His Cys Tyr Val Asp Thr Glu Val Glu Met Lys Glu Ile
65                  70                  75                  80

<210> SEQ ID NO 6
<211> LENGTH: 20
<212> TYPE: PRT
<213> ORGANISM: Homo sapiens

<400> SEQUENCE: 6

Asn Val Tyr Thr Glu Ile Lys Cys Asn Ser Leu Leu Pro Leu Ala Ala
1               5                   10                  15

Ile Val Arg Val
            20

<210> SEQ ID NO 7
<211> LENGTH: 20
<212> TYPE: PRT
<213> ORGANISM: Homo sapiens

<400> SEQUENCE: 7

Asn Val Tyr Thr Glu Ile Lys Cys Asn Ser Leu Leu Pro Leu Glu Glu
1               5                   10                  15

Ile Val Arg Val
            20

<210> SEQ ID NO 8
<211> LENGTH: 25
<212> TYPE: PRT
<213> ORGANISM: Homo sapiens

```
<400> SEQUENCE: 8

Arg Thr Gly Tyr Asp Asn Arg Glu Ile Val Met Lys Tyr Ile His Tyr
1               5                   10                  15

Lys Leu Ser Gln Arg Gly Tyr Glu Trp
            20                  25

<210> SEQ ID NO 9
<211> LENGTH: 25
<212> TYPE: PRT
<213> ORGANISM: Homo sapiens

<400> SEQUENCE: 9

Trp Tyr Glu Lys Gln Arg Ser Leu His Gly Ile Met Tyr Val Ile
1               5                   10                  15

Glu Asp Arg Asn Thr Lys Gly Tyr Arg
            20                  25

<210> SEQ ID NO 10
<211> LENGTH: 31
<212> TYPE: PRT
<213> ORGANISM: Homo sapiens

<400> SEQUENCE: 10

Arg Lys Lys Arg Arg Gln Arg Arg Arg Gly Gly Asn Val Tyr Thr Glu
1               5                   10                  15

Ile Lys Cys Asn Ser Leu Leu Pro Leu Asp Asp Ile Val Arg Val
            20                  25                  30

<210> SEQ ID NO 11
<211> LENGTH: 31
<212> TYPE: PRT
<213> ORGANISM: Homo sapiens

<400> SEQUENCE: 11

Arg Lys Lys Arg Arg Gln Arg Arg Arg Gly Gly Asp Leu Asn Glu Val
1               5                   10                  15

Thr Cys Ser Leu Ile Val Asp Arg Ile Asn Pro Val Lys Leu Tyr
            20                  25                  30

<210> SEQ ID NO 12
<211> LENGTH: 31
<212> TYPE: PRT
<213> ORGANISM: Homo sapiens

<400> SEQUENCE: 12

Arg Lys Lys Arg Arg Gln Arg Arg Arg Gly Gly Asn Val Tyr Thr Glu
1               5                   10                  15

Ile Lys Cys Asn Ser Leu Leu Pro Leu Ala Ala Ile Val Arg Val
            20                  25                  30
```

INHIBITORS OF BCL-2

RELATED APPLICATION

This application is a National Phase filing of PCT/US2011/050183, filed Sep. 1, 2011, which claims priority from U.S. Provisional Application No. 61/379,167, filed Sep. 1, 2010, the subject matter of which are incorporated herein by reference in their entirety.

GOVERNMENT FUNDING

This application was made with government support under Grant No. NIH/NCI RO01 085804 and NIH/NCI SPN00583 awarded by National Institutes of Health. The government has certain rights in the invention.

TECHNICAL FIELD

This application relates generally to compounds, and, more particularly, to polypeptides, proteins, and nucleic acids encoding such polypeptides and proteins that can be used to inhibit the interaction of Bcl-2 to the inositol 1,4,5-triphosphate receptor ($IP_3R$).

BACKGROUND OF THE INVENTION

Apoptosis is an important process in the development of cells and is important in maintaining the proper number of cells in the body. Candidates for apoptosis include cells that may be a danger to an organism, such as cells with damaged DNA or cells growing at improper rates. However, apoptosis is also applied to normal cells that have simply become obsolete as organisms grow and develop.

Bcl-2 protein is known to inhibit apoptotic cell death. Bcl-2 protein serves as a check on apoptosis allowing healthy and useful cells to survive. Anti-apoptotic molecules, such as Bcl-2 are often overexpressed in cancer cells and their inhibition is an attractive target for selective killing of tumor cells via induction of apoptosis. Bcl-2 overexpression and/or activation has been correlated with resistance to chemotherapy, to radiotherapy and to development of hormone-resistant tumors Inhibition of apoptosis by Bcl-2 contributes to cancer by inhibiting cell death. Thus, inhibiting Bcl-2 activity in cancer cells can reduce chemotherapeutic resistance and increase the killing of cancer cells.

The Bcl-2 gene was discovered as the translocated locus in a B-cell leukemia. Bcl-2 contains a single transmembrane domain and is localized within a cell to the outer mitochondrial, nuclear, and endoplasmic reticulum membranes. Bcl-2 was first isolated as a breakpoint rearrangement in human follicular lymphomas. In humans, most follicular B-cell lymphomas contain a chromosomal translocation that moves the gene for Bcl-2 from its normal location to a position within the genes for immunoglobulins. In this new location, higher quantities of Bcl-2 are produced. Since Bcl-2 is a potent pro-survival protein, it shields the cancer cells from apoptotic instruction.

The effector molecules in the apoptotic pathway are a family of enzymes known as the caspases. The Bcl-2 protein suppresses apoptosis by preventing the activation of the caspases that carry out the process. Caspase enzymes are cystein proteases that selectively cleave proteins at sites just C-terminal to aspartate residues. These proteases have specific intracellular targets such as proteins of the nuclear lamina and cytoskeleton. The cleavage of these substrates leads to the demise of a cell.

The inositol 1,4,5-triphosphate ($IP_3$) messenger molecule is water soluble, and can diffuse within the cytosol carrying an activated G protein signal from the cell surface to the endoplasmic reticulum (ER) surface. $IP_3$ binds to an $IP_3R$ and induces opening of the channel allowing $Ca^{2+}$ ions to exit from the ER into the cytosol. The released calcium then triggers a mass exodus of cytochrome c from all mitochondria in the cell, thus activating the caspase and nuclease enzymes that finalize the apoptotic process.

It has previously been shown that Bcl-2 interacts with the inositol 1,4,5-triphosphate receptor ($IP_3R$) and inhibits $IP_3$-mediated $Ca^{2+}$ release from the ER, thereby inhibiting anti-CD3 induced apoptosis in immature T cells (JCB 166: 193-203, 2004; JCB 172: 127-137, 2006). $IP_3R$ have a broad tissue distribution and are mostly found in the cell integrated into the endoplasmic reticulum. The $IP_3R$ is a large six transmembrane ligand gated ion channel which mainly transmits calcium ions and thereby facilitates triggers apoptosis.

SUMMARY OF THE INVENTION

This application relates to a polypeptide that inhibits binding of Bcl-2 to $IP_3$ receptors ($IP_3R$) of cells that express $IP_3R$ and Bcl-2. The polypeptide comprises an amino acid sequence that includes about 10 to 80 amino acids. The amino acid sequence has a sequence identity that is at least 80% homologous to about 10 to 80 consecutive amino acids of SEQ ID NO:1. The about 10 to 80 consecutive amino acids of SEQ ID NO: 1 includes at least one aspartic acid. The polypeptide, unlike the consecutive amino acids of SEQ ID NO: 1, has at least one aspartic acid of the amino acid sequence substituted with an amino acid residue that is resistant to protease cleavage. In some aspects, the amino acid that is resistant to protease cleavage can include alanine or glutamic acid. In other aspects, the polypeptide can include an amino acid sequence having a sequence identity selected from the group consisting of SEQ ID NOs: 2, 3, 4, 5, 6, 7, and 12. In still other aspects, the polypeptide can further include an amino acid sequence that facilitates transport of the purified peptide across a biological membrane.

This application also relates to a pharmaceutical composition comprising a therapeutically effective amount of a polypeptide that inhibits binding of Bcl-2 to $IP_3$ receptors ($IP_3R$) of cells that express $IP_3R$ and Bcl-2 and pharmaceutically effective carrier. The polypeptide comprises an amino acid sequence that includes about 10 to 80 amino acids. The amino acid sequence has a sequence identity that is at least 80% homologous to about 10 to 80 consecutive amino acids of SEQ ID NO:1. The about 10 to 80 consecutive amino acids of SEQ ID NO: 1 includes at least one aspartic acid. The polypeptide, unlike the consecutive amino acids of SEQ ID NO: 1, has at least one aspartic acid of the amino acid sequence substituted with an amino acid residue that is resistant to protease cleavage. In some aspects, the amino acid that is resistant to protease cleavage can include alanine or glutamic acid. In other aspects, the polypeptide can include an amino acid sequence having a sequence identity selected from the group consisting of SEQ ID NOs: 2, 3, 4, 5, 6, 7, and 12. In still other aspects, the polypeptide can further include an amino acid sequence that facilitates transport of the purified peptide across a biological membrane.

In yet another aspect, the pharmaceutical composition can include a second agent that inhibits binding of Bcl-2 to BH3 proapoptotic proteins. The second agent can include at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin. The second agent can also include N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzenesulfonamide or ABT-737.

The application further relates to a method of inducing apoptosis in a cell expressing Bcl-2 and $IP_3R$. The method includes administering to the cell a therapeutically effective amount of a polypeptide that inhibits binding of Bcl-2 to $IP_3$ receptors ($IP_3R$) of cells that express $IP_3R$ and Bcl-2. The polypeptide comprises an amino acid sequence that includes about 10 to 80 amino acids. The amino acid sequence has a sequence identity that is at least 80% homologous to about 10 to 80 consecutive amino acids of SEQ ID NO:1. The about 10 to 80 consecutive amino acids of SEQ ID NO: 1 includes at least one aspartic acid. The polypeptide, unlike the consecutive amino acids of SEQ ID NO: 1, has at least one aspartic acid of the amino acid sequence substituted with an amino acid residue that is resistant to protease cleavage. In some aspects, the amino acid that is resistant to protease cleavage can include alanine or glutamic acid. In other aspects, the polypeptide can include an amino acid sequence having a sequence identity selected from the group consisting of SEQ ID NOs: 2, 3, 4, 5, 6, 7, and 12. In still other aspects, the polypeptide can further include an amino acid sequence that facilitates transport of the purified peptide across a biological membrane.

The method can further include administering a second agent to the cell that inhibits binding of Bcl-2 to BH3 pro-apoptotic proteins. The second agent can include at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin. The second agent can also include N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzenesulfonamide or ABT-737.

The application further relates to a method of treating a neoplastic order, such as chronic lymphocytic leukemia or multiple myeloma, in a subject. The method includes administering to neoplastic cells of the subject expressing $IP_3R$ and Bcl-2 a therapeutically effective amount of a polypeptide that inhibits binding of Bcl-2 to $IP_3$ receptors ($IP_3R$) of cells that express $IP_3R$ and Bcl-2. The polypeptide comprises an amino acid sequence that includes about 10 to 80 amino acids. The amino acid sequence has a sequence identity that is at least 80% homologous to about 10 to 80 consecutive amino acids of SEQ ID NO:1. The about 10 to 80 consecutive amino acids of SEQ ID NO: 1 includes at least one aspartic acid. The polypeptide, unlike the consecutive amino acids of SEQ ID NO: 1, has at least one aspartic acid of the amino acid sequence substituted with an amino acid residue that is resistant to protease cleavage. In some aspects, the amino acid that is resistant to protease cleavage can include alanine or glutamic acid. In other aspects, the polypeptide can include an amino acid sequence having a sequence identity selected from the group consisting of SEQ ID NOs: 2, 3, 4, 5, 6, 7, and 12. In still other aspects, the polypeptide can further include an amino acid sequence that facilitates transport of the purified peptide across a biological membrane.

The method can further include administering a second agent to the neoplastic cells that inhibits binding of Bcl-2 to BH3 pro-apoptotic proteins. The second agent can include at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin. The second agent can also include N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzenesulfonamide or ABT-737.

BRIEF DESCRIPTION OF DRAWINGS

Further features of the present invention will become apparent to those skilled in the art to which the present invention relates from reading the following description of the invention with reference to the accompanying drawings.

FIG. 8 illustrates charts showing (A) percent inhibition of peptide (10 μM)-induced $Ca^{2+}$ oscillations by the $IP_3R$ inhibitor xestospongin C (10 μM) or the phospholipase C inhibitor U73122 (0.25 μM) in Jurkat cells, based on the percentage of cells displaying $Ca^{2+}$ oscillations during 90 min single cell recordings (mean±SE, 3 experiments, average 85 cells analyzed per treatment condition per experiment); (B) representative single cell $Ca^{2+}$ recordings illustrating $Ca^{2+}$ responses to 5 μM peptide addition (arrow) in wild type DT40 cells; and (C) percentage of wild type WT and TKO DT40 cells displaying $Ca^{2+}$ oscillations in response to treatment with 5 μM peptides (mean±SE, 4 experiments, average 60 cells analyzed per recording).

FIG. 11 illustrates charts showing the failure of ABT-737 to induce $Ca^{2+}$ elevation: (A) percentage of CLL cells with $Ca^{2+}$ oscillations in response to 5 μM TAT-Scr or TAT-IDP, or 2 μM ABT-737, with symbols representing the mean±SE in 2 experiments (average 80 cells per experiment); and (B) cell death (trypan blue dye uptake) in CLL cells incubated with or without 2 μM ABT-737 for 24 hr, with symbols representing the mean±SE in 7 experiments (average 400 cells counted per individual treatment).

DETAILED DESCRIPTION

Figure 1:
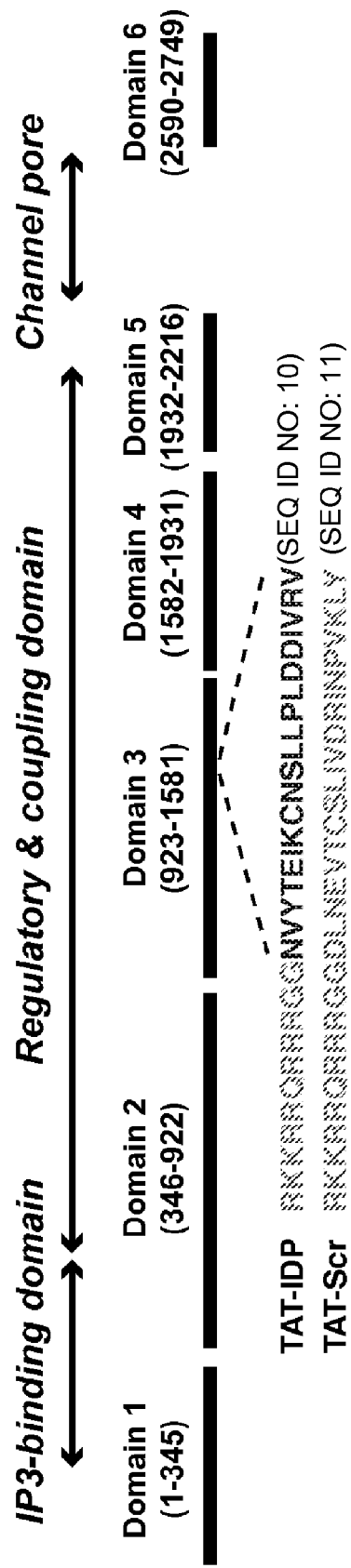
FIG. 1 illustrates a diagram of type 1 $IP_3R$ domains, designating the origin of the IDP sequence (SEQ ID NO: 10) and scrambled control sequence (SEQ ID NO: 11), along with the TAT sequence.

The following definitions are set forth to illustrate and define the meaning and scope of the various terms used to describe the invention herein.

As used herein, the term "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

As used herein, the terms "peptide(s)", "protein(s)" and "polypeptide(s)" are used interchangeably herein.

As used herein, the terms "polynucleotide sequence" and "nucleotide sequence" are also used interchangeably herein.

As used herein, the term "recombinant" refers to a protein is derived from a prokaryotic or eukaryotic expression system.

As used herein, the term "wild type" refers to the naturally occurring polynucleotide sequence encoding a protein, or a portion thereof, or protein sequence, or portion thereof, respectively, as it normally exists in vivo.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Vectors can include those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue. The term also covers so-called "leaky" promoters, which regulate expression of a selected nucleic acid primarily in one tissue, but cause expression in other tissues as well.

As used herein, the terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

As used herein, the terms "chimeric protein" or "fusion protein" refer to a fusion of a first amino acid sequence encoding a polypeptide with a second amino acid sequence defining a domain (e.g., polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

As used herein, "non-human animals" include mammals such as rats, mice, rabbits, sheep, cats, dogs, cows, pigs, and non-human primates.

As used herein, the terms "isolated" or "purified" with respect to polypeptides or nucleic acids, refers to molecules separated from other polypeptides or nucleic acids, respectively, that are present in the natural source of the macromolecule. The term isolated or purified as used herein also refers to a nucleic acid or peptide that is substantially free of cellular material, or culture medium when produced by recombinant DNA techniques, or chemical precursors or other chemicals when chemically synthesized.

As used herein, the phrases "parenteral administration" and "administered parenterally" refers to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the phrases "systemic administration," "administered systemically," "peripheral administration" and "administered peripherally" refers to the administration other than directly into or locally to the tissue being treated, such that it enters the animal's system and, thus, is subject to metabolism and other like processes, for example, subcutaneous administration.

As used herein, the phrase "effective amount" refers to the amount of one or more agent, material, or composition comprising one or more agents as described herein which is effective for producing some desired effect in a subject; for example, an amount of the compositions described herein effective to promote apoptosis.

As used herein, the term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All stereoisomers are included within the scope of the present invention.

As used herein, the phrase "therapeutically- or pharmaceutically-effective amount" as applied to the disclosed compositions refers to the amount of composition sufficient to induce a desired biological result. That result can be alleviation of the signs, symptoms, or causes of a disease, or any other desired alteration of a biological system. For example, the result can involve a decrease and/or reversal of cancerous cell growth.

As used herein, the phrase "resistant to protease cleavage" with respect to a substituted amino acid in an amino acid sequence, it is meant that the amino acid residue that is substituted for a native or original amino acid or the polypeptide with the substituted amino acid is at least 10%, 20%, 30%, 40%, 50%, 60%, 70%, 80%, or 90% more resistant to protease cleavage that native or original amino acid residue or the polypeptide including the native or original amino acid residue.

This application relates generally to purified and isolated polypeptides, A pharmaceutical composition comprising the polypeptides, the use of the polypeptides in methods of substantially inhibiting Bcl-2 binding to inositol 1,4,5-triphosphate receptors ($IP_3R$), and the use of the polypeptides in methods of inducing apoptosis in cells expressing Bcl-2 and $IP_3R$, particularly to inducing apoptosis, in neoplastic cells (e.g., cancer cells, such as chronic lymphocytic leukemia or multiple myeloma) expressing Bcl-2 and $IP_3R$.

As used herein, the terms "inhibit", "inhibiting", or "inhibition" includes any measurable reproducible substantial reduction in the interaction between Bcl-2 and $IP_3R$, cancer, or any other activities Bcl-2 may mediate. A substantial reduction is a "reproducible", i.e., consistently observed, reduction in binding.

It was found that Bcl-2 interacts directly with the activation coupling domain of the $IP_3R$ from 1347 aa to 1426 aa. This internal coupling domain transfers the ligand binding signal from the N-terminal $IP_3$ binding domain to the C-terminal channel domain. The coupling domain is necessary to keep the $IP_3R$ channel closed and regulates the activity of the $IP_3R$ by binding to regulatory proteins. By binding to this region, Bcl-2 exerts its regulatory effect on $IP_3$-mediated $Ca^{2+}$ signals.

It was also found that polypeptides derived from the specific Bcl-2-interacting domain of $IP_3R$, such as a BH4 domain binding peptide including a portion of amino acid SEQ ID NO:1, can mimic $IP_3R$'s binding effect and when administered to a neoplastic cell expressing Bcl-2 and $IP_3R$ induce apoptosis and/or necrosis in the neoplastic cell. It was further found that aspartic acid residues of these polypeptides (i.e., native or unsubstituted polypeptides), which include an amino acid sequence that is homologous to at least about 10 consecutive amino acids of SEQ ID NO: 1 and at least on aspartic acid residue are susceptible to aspartyl protease cleavage.

Unexpectedly, it was found that substitution of aspartic acid residues of the polypeptide with an amino acid residue that is more resistant to protease cleavage than aspartic acid and that still allowed the polypeptide to maintain its conformation allowed for greater intracellular accumulation of the substituted polypeptides in neoplastic cells and enhanced Ca+ elevation in neoplastic cells (e.g., chronic lymphocytic leukemia cells) compared to the native or unsubstituted polypeptides as well as an enhanced apoptosis of the neoplastic cells.

Accordingly, an aspect of the application relates to an isolated and/or purified polypeptide that inhibits binding of Bcl-2 and $IP_3R$ and is resistant to protease cleavage. The protease resistant polypeptide can include an amino acid sequence that comprises about 10 to 80 amino acids (e.g., about 10 to 30 amino acids) and has a sequence identity that is at least 80% homologous to about 10 to 80 consecutive amino acids of SEQ ID NO:1 ERDRMDENSPLMYHI-HLVELLAVCTEGKNVYTEIKCNSLLPLDDIVRV-VTHEDCIPEV KIAYINFLNHCYVDTEVEMKEI (SEQ ID NO:1). The about 10 to 80 consecutive amino acids of SEQ ID NO: 1 includes at least one aspartic acid. The amino acid sequence of the protease resistant polypeptide, unlike the consecutive amino acids of SEQ ID NO: 1, has at least one aspartic acid of the amino acid sequence substituted with an amino acid residue that is resistant to protease cleavage. In some aspects, the amino acid that is resistant to protease cleavage can include alanine or glutamic acid.

Examples of protease resistant polypeptides and/or protease resistant amino acids that can be used in accordance with the compositions or methods described herein can have an amino acid sequence selected from the group consisting of:

```
                                              (SEQ ID NO: 2)
ERARMAENSPLMYHIHLVELLAVCTEGKNVYTEIKCNSLLPLAAIVRVVT

HEDCIPEVKIAYINFLNHCYVATEVEMKEI, (SEQ ID NO: 3)
ERDRMDENSPLMYHIHLVELLAVCTEGKNVYTEIKCNSLLPLAAIVRVVT

HEDCIPEVKIAYINFLNHCYVDTEVEMKEI, (SEQ ID NO: 4)
ERERMEENSPLMYHIHLVELLAVCTEGKNVYTEIKCNSLLPLEEIVRVVT

HEDCIPEVKIAYINFLNHCYVETEVEMKEI, (SEQ ID NO: 5)
ERDRMDENSPLMYHIHLVELLAVCTEGKNVYTEIKCNSLLPLEEIVRVVT

HEDCIPEVKIAYINFLNHCYVDTEVEMKEI, (SEQ ID NO: 6)
NVYTEIKCNSLLPLAAIVRV,
and (SEQ ID NO: 7)
NVYTEIKCNSLLPLEEIVRV.
```

The protease resistant Bcl-2/IP$_3$R inhibiting polypeptides and/or amino acid sequences described herein can be substantially free of other proteins or pathological agents. These polypeptides can also be a product of mammalian cells, or the product of chemical synthetic procedures or of prokaryotic or eukaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or prokaryote (e.g., *E. coli*) host cells are free of association with any mammalian proteins. The products of expression in vertebrate cells (e.g., non-human mammalian (COS or CHO) and avian) are free of association with any human proteins. Depending upon the host employed, and other factors, polypeptides described herein may be glycosylated with mammalian or other eukaryotic carbohydrates or may be non-glycosylated. The protease resistant Bcl-2/IP$_3$R inhibiting polypeptides and/or amino acid sequences described herein may also include an initial methionine amino acid residue (at position −1 with respect to the first amino acid residue of the polypeptide.)

It will be appreciated that biologically functional equivalents, or even improvements, of the protease resistant Bcl-2/IP$_3$R inhibiting polypeptides and/or amino acid sequences can be made. Modifications and changes may be made in the structure of such a polypeptide and still obtain a molecule having like or otherwise desirable characteristics. For example, certain amino acids in the polypeptide structure may be substituted without appreciable loss of interactive binding capacity.

Since it is the interactive capacity and nature of a polypeptide that defines that protein's biological functional activity, certain amino acid sequence substitutions can be made in an amino acid sequence (or of course, the underlying DNA sequence) and nevertheless obtain a polypeptide with like properties. It is thus contemplated that various changes may be made in the sequence of the protease resistant Bcl-2/$IP_3R$ inhibiting polypeptides and/or amino acid sequences without appreciable loss of their biological utility or activity (e.g., the peptides ability to inhibit binding of Bcl-2 to $IP_3R$).

It is also well understood by the skilled artisan that, inherent in the definition of a "biologically functional equivalent" protein or polypeptide, is the concept that there is a limit to the number of changes that may be made within a defined portion of the molecule and still result in a molecule with an acceptable level of equivalent biological activity. Biologically functional equivalent proteins and polypeptides are thus defined herein as those proteins and polypeptides in which certain, not most or all, of the amino acids may be substituted. Of course, a plurality of distinct proteins/polypeptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine; are defined herein as biologically functional equivalents.

Following the procedures noted in the published application by Alton et al. (WO83/04053), one can readily design and manufacture genes coding for microbial expression of peptides having primary conformations, which differ from that herein specified in terms of the identity of location of one or more residues (e.g., substitutions, terminal and intermediate additions and deletions). Alternately, modification of cDNA may be readily accomplished by well-known site-directed mutagenesis techniques and employed to generate analogs and derivatives of the polypeptide. Such products would share at least one of the biological properties of the protease resistant Bcl-2/$IP_3R$ inhibiting polypeptides and/or amino acid sequences but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells.

The protease resistant Bcl-2/$IP_3R$ inhibiting polypeptides and/or amino acid sequences described herein can also be in the form of a conjugate protein or drug delivery construct having a transport subdomain(s) or moiety(ies) (i.e., transport moieties). The transport moieties can facilitate uptake of the polypeptide into a mammalian (i.e., human or animal) tissue or cell. The transport moieties can be covalently linked to the substituted amino acid sequence described herein. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the peptide.

The transport moieties can be repeated more than once in the polypeptide. The repetition of a transport moiety may affect (e.g., increase) the uptake of the polypeptide by a desired cell. The transport moiety may also be located either at the amino-terminal region of the amino acid sequence or at its carboxy-terminal region or at both regions.

In an aspect of the invention, the transport moiety can include at least one transport peptide sequence that allows the polypeptide to penetrate into the cell by a receptor-independent mechanism. Examples of transport sequences that can be used include a Tat-mediated protein delivery sequence (Vives (1997) 272: 16010-16017), polyargine sequences (Wender et al. 2000, PNAS 24: 13003-13008) and antennapedia (Derossi (1996) J. Biol. Chem. 271: 18188-18193). Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety. Still other examples of transport moieties include conjugates containing amino acids of Tat HIV protein, herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

In addition, the transport moiety(ies) can include polypeptides having a basic amino acid rich region covalently linked to the protease resistant Bcl-2/$IP_3R$ inhibiting polypeptides and/or amino acid sequences. As used herein, the term "basic amino acid rich region" relates to a region of a protein with a high content of the basic amino acids such as arginine, histidine, asparagine, glutamine, lysine. A "basic amino acid rich region" may have, for example 15% or more (up to 100%) of basic amino acids. In some instance, a "basic amino acid rich region" may have less than 15% of basic amino acids and still function as a transport agent region. In one example, a basic amino acid region will have 30% or more (up to 100%) of basic amino acids.

In one example, the protease resistant Bcl-2/$IP_3R$ inhibiting polypeptide can be provided as a fusion protein (polypeptide) that includes of a carboxy terminal protease resistant Bcl-2/$IP_3R$ inhibiting amino acid sequence in accordance with the application and an amino terminal transport moiety. The amino terminal transport moiety can be a transport subdomain of HIV (e.g., HIV-1) Tat protein, homeoprotein transport sequence, a Histidine tag or a functional derivative and analogues thereof (i.e. pharmaceutically acceptable chemical equivalents thereof). In another example, the fusion protein (polypeptide) can include a carboxy terminal protease resistant Bcl-2/$IP_3R$ inhibiting polypeptide and an amino terminal transport moiety that includes a homeodomain of antennapedia.

In another aspect of the application, the protease resistant Bcl-2/$IP_3R$ inhibiting polypeptide and/or amino acid sequence can be non-covalently linked to a transport moiety or transfection agent. An example of a non-covalently linked peptide transfection agent is the Chariot protein delivery system (See U.S. Pat. No. 6,841,535; Morris et al. (1999) J. Biol. Chem. 274(35):24941-24946; and Morris et al. (2001) Nature Biotech. 19:1173-1176), all herein incorporated by reference in their entirety.

The Chariot protein delivery system includes a peptide transfection agent that can non-covalently complex with the Bcl-2/$IP_3R$ inhibiting amino acid sequence described herein. Upon cellular internalization, the transfection agent dissociates and the Bcl-2/$IP_3R$ inhibiting amino acid sequence is free to function. The complex of the Chariot transfection peptide and the Bcl-2/$IP_3R$ inhibiting amino acid sequence can be delivered to and internalized by mammalian cells allowing for higher dosages of therapeutics to be delivered to the site of pathology.

In accordance with another aspect of the present invention, the protease resistant Bcl-2/$IP_3R$ inhibiting polypeptide and/or amino acid sequence can be provided in a pharmaceutically acceptable carrier. The pharmaceutical compositions will generally comprise an effective amount of the protease resistant Bcl-2/$IP_3R$ inhibiting polypeptide and/or amino acid sequence, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

The protease resistant Bcl-2/$IP_3R$ inhibiting polypeptide and/or amino acid sequence will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such a polypeptide or immunoconjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the protease resistant Bcl-2/$IP_3R$ inhibiting polypeptide and/or amino acid sequence can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers can include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the protease resistant Bcl-2/IP$_3$R inhibiting polypeptide and/or amino acid sequence can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

Pharmaceutical compositions can generally include an amount of the protease resistant Bcl-2/IP$_3$R inhibiting polypeptide and/or amino acid sequence admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of polypeptides comprising the protease resistant Bcl-2/IP$_3$R inhibiting polypeptide and/or amino acid sequence are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver the protease resistant Bcl-2/$IP_3R$ inhibiting polypeptide and/or amino acid sequence in accordance with the present invention. The slow release formulations are typically implanted in the vicinity of the disease site, for example, at the site of a tumor.

Examples of sustained-release preparations include semi-permeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and y ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the Bcl-2/$IP_3R$ inhibiting polypeptide. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

A population of cells or tissues that express IP$_3$R can and Bcl-2 thus be contacted with a biologically or therapeutically effective amount of the protease resistant Bcl-2/IP$_3$R inhibiting polypeptide and/or amino acid sequence in a pharmaceutical carrier under conditions effective to substantially inhibit Bcl-2 binding to IP$_3$R.

A further aspect of the present invention relates to nucleic acid sequences useful in facilitating expression in prokaryotic or eukaryotic host cells of the protease resistant Bcl-2/IP$_3$R inhibiting polypeptide and/or amino acid sequence. Such nucleic acid molecules may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. There may also be multiple coding sequences that, as a result of the redundancy or degeneracy of the genetic code, encodes the same polypeptide as such polynucleotides.

Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamine or aspartine; or (d) a residue having a bulky side chain, e.g., phenylalanine, for (or by) one not having a side chain, e.g., glycine.

Shorter oligonucleotides that encode or hybridize with nucleic acids that encode fragments of polypeptide can be used as probes, primers, or antisense molecules. Longer polynucleotides that encode or hybridize with nucleic acids that encode fragments of the polypeptide can also be used in various aspects of the invention. Nucleic acids encoding fragments of the polypeptide can be made by enzymatic digestion (e.g., using a restriction enzyme) or chemical degradation of the full-length polypeptide.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding a polypeptide conjugate, such as a fusion protein, may also be used in the invention. Such nucleic acids can be made by preparing a construct (e.g., an expression vector) that expresses the polypeptide fusion protein when introduced into a suitable host. For example, such a construct can be made by ligating a first polynucleotide encoding the polypeptide fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents. (See, e.g., Zon (1988) Pharm. Res. 5:539-549). To this end, the oligonucleotides may be conjugated to another molecule, e.g., a peptide, hybridization triggered cross-linking agent, transport agent, hybridization-triggered cleavage agent, etc.

The DNA sequences provided by the invention are useful in generating new and useful viral and circular plasmid DNA vectors, new and useful transformed and transfected prokaryotic and eukaryotic host cells (including bacterial and yeast cells and mammalian cells grown in culture), and new and useful methods for cultured growth of such host cells capable of expression of the Bcl-2/IP$_3$R inhibiting polypeptide and its related products.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

In accordance with another aspect of the present invention, the protease resistant Bcl-2/IP$_3$R inhibiting polypeptide and/or amino acid sequence may be used to treat animals, patients, or subjects with a number of neoplastic diseases, including but not limited to lymphoma (e.g., follicular B-cell lymphoma), leukemia (chronic lymphocytic leukemia), multiple myelsoma, melanoma, breast, prostate, and lung carcinomas. The protease resistant Bcl-2/IP$_3$R inhibiting polypeptide and/or amino acid sequence can also be used for reducing resistance to conventional cancer treatment.

In designing appropriate doses of the protease resistant Bcl-2/IP$_3$R inhibiting polypeptide and/or amino acid sequence for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m$^2$) between the experimental animal and the human patient. All such calculations are well known and routine to those of ordinary skill in the art.

The intention of the therapeutic regimens described herein is generally to produce significant anti-neoplastic effects while still keeping the dose below the levels associated with unacceptable toxicity. In addition to varying the dose itself, the administration regimen can also be adapted to optimize the treatment strategy. In administering the particular doses, one can provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated. In certain embodiments, the agent can be delivered to cancer cells by site-specific means.

Cell-type-specific delivery can be provided by coupling or conjugating the protease resistant Bcl-2/IP$_3$R inhibiting polypeptide and/or amino acid sequence to a targeting moiety, for example, one that selectively binds to cancer cells expressing the a marker, protein, or epitope that is specific for the cancer cell. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In one embodiment, the targeting moiety that is coupled or conjugated to the therapeutic agent can include a peptide, targeting peptide, or antibody that binds to and/or complexes with a leukemia cell. Such antibodies are disclosed for example in U.S. Pat. Nos. 6,187,287 and 6,790,827 as well as U.S. Patent Application Publication Nos. 2011/0189095, 2011/0110931, and 2011/0015090, all of which are incorporated by reference in their entirety.

In another embodiment, the targeting peptide and the protease resistant Bcl-2/IP$_3$R inhibiting polypeptide and/or amino acid sequence can be conjugated onto a nanoparticle. Nanoparticles are a new class of drug carriers with precisely defined nanosize (2-5 nm). These carriers have compact molecular morphology and high surface functionalities for effective conjugation of targeted agents, therapeutic agents and imaging agents. In one example, the nanoparticle can have a size (e.g., about 3 nm) that allows effective transport and distribution of the targeted delivery systems in solid or systemic tumors, carcinomas, leukemias, or cancers.

The targeting peptide can be conjugated to the surface of the nanoparticle via, for example, a PEG spacer (e.g., 1,000 Da) to a functional group pre-conjugated to the nanoparticle. The PEG spacer is designed to reduce the steric hindrance of the drug carrier and to achieve effective specific binding to the target. The protease resistant Bcl-2/IP$_3$R inhibiting polypeptide and/or amino acid sequence can be conjugated to the nanoparticle via, for example, a disulfide spacer. The disulfide spacer can be designed to release the protease resistant Bcl-2/IP$_3$R inhibiting polypeptide and/or amino acid sequence in the cytoplasm, which has a high concentration of reductive glutathione (e.g., about 3 mM). The disulfide spacer can be readily reduced by cytoplasmic glutathione to release the therapeutic peptide inside cancer cells.

In some embodiments, the nanoparticle comprising the protease resistant Bcl-2/IP$_3$R inhibiting polypeptide and/or amino acid sequence and targeting peptide can be directly or indirectly labeled with a detectable moiety or imaging agent. The role of a detectable moiety is to facilitate the detection step of a nanoparticle by allowing visualization of the complex formed by binding of the targeting peptide to the cancer cell. The detectable moiety can be selected such that it generates a signal, which can be measured and whose intensity is related (preferably proportional) to the amount of the nanoparticle bound to the tissue being treated. Methods for labeling biological molecules, such as polypeptides and antibodies are well-known in the art (see for example, *Methods in Enzymol.*, 1974, Vol. 34, Academic Press: New York, N.Y.; and, *Anal. Biochem.*, 1988, 171: 1-32).

Distinct detectable moieties can be used to practice different embodiments. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some embodiments, the nanoparticles described herein may be used in conjunction with non-invasive imaging (e.g., neuroimaging) techniques for in vivo imaging of the molecular probe, such as magnetic resonance spectroscopy (MRS) or imaging (MRI), or gamma imaging, such as positron emission tomography (PET) or single-photon emission computed tomography (SPECT). The term "in vivo imaging" refers to a method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

The protease resistant Bcl-2/IP$_3$R inhibiting polypeptide and/or amino acid sequence may also be delivered in combination with a second agent that induces apoptosis in neoplastic cells. Although many anti-cancer agents may have, as part of their mechanism of action, an apoptosis-inducing effect, certain agents have been discovered, designed or selected with this as a primary mechanism, as described below.

In an aspect of the invention, the second agent can be a small-molecule inhibitor that directly binds Bcl-2/IP$_3$R or related antiapoptotic proteins and inhibits the Bcl-2-BH3 domain binding to BH3 domain proteins or BH3 only molecules, such as BID, NOXA, PUMA, BIK, BIM, and BAD (i.e., a Bcl-2/BH3 inhibitor). By targeting two different regions of Bcl-2 involved in apoptosis inhibition with the Bcl-2/IP$_3$R peptide of the present invention and an inhibitor of Bcl-2 to BH3 domain proteins, the proapoptotic activity of the Bcl-2/BH3 inhibitors and the Bcl-2/IP$_3$R peptides are enhanced.

One example of a small molecule inhibitor is gossypol or 1,6,7,1',6',7'-Hexahydroxy-5,5'-diisopropyl-3,3'-dimethyl-[2,2']binaphthalenyl-8,8'-dicarbaldehyde. Gossypol has the following formula:

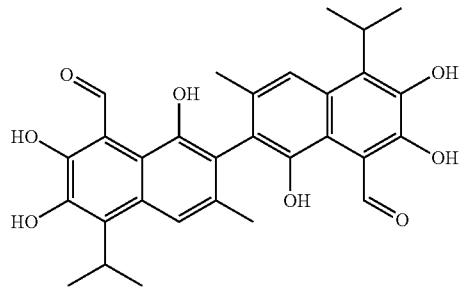 [SMILES: Cc1cc2c(C(C)C)c(O)c(O)c(C=O)c2c(O)c1-c1c(C)cc2c(C(C)C)c(O)c(O)c(C=O)c2c1O]

Gossypol is found in cottonseeds originally used as an herbal medicine in China. Gossypol binds via a conserved 16 amino acid motif called a Bcl-2 homology-3 (BH3)

domain found on the surface of antiapoptotic Bcl-2 family proteins. This binding pocket represents a regulatory site, where endogenous antagonists dock onto Bcl-2 and related antiapoptotic proteins, negating their cytoprotective activity. Proof of concept experiments using BH3 peptides have suggested that compounds docking at this regulatory site on Bcl-2 and Bcl-XL effectively promote apoptosis of lymphoma and leukemia cells in vivo in mice.

Gossypol interacts with the BH3-binding pockets of 4 antiapoptotic Bcl-2 family proteins tested to date, Bcl-2, Bcl-$X_L$, Bcl-B, and Bfl-1, displacing BH3 peptides with an inhibitory concentration of 50% ($IC_{50}$) of about 0.5 µM.

Another example of small molecule inhibitor of Bcl-2 is a semisynthetic analog of gossypol known as apogossypol or 5,5'-Diisopropyl-3,3'-dimethyl-[2,2']binaphthalenyl-1,6,7,1',6',7'-hexaol, which has the following general formula:

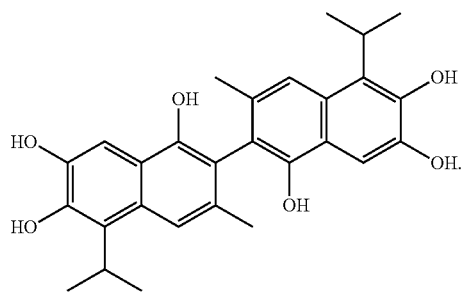

Other examples of chemical inhibitors of Bcl-2, Bcl-$X_L$, and Mcl-1 have been reported, most of which are currently in preclinical evaluation, including: chromenes or chromene derivatives, such as HA14-1 or 2-amino-6-bromo-4-cyanoethoxycarbonyl-methyl)-4H-chromene-3-carboxylic acid ethyl ester or other compounds disclosed in U.S. Pat. No. 6,492,389; thiazolidins or thiazolidin derivatives, such as BH3I -1 or (2-[5-(4-Bromo-benzylidene)-4-oxo-2-thioxo-thiazolidin-3-yl]-3-methyl-butyric acid); benzene sulfonyl derivatives, such as BH3I -2 or (5-chloro-N-[2-chloro-4-(4-chloro-benzenesulfonyl)-phenyl]-2-hydroxy-3-iodo-benzamide); antimycin analogs, such as 3-(3-Formylamino-2-hydroxy-benzoylamino)-2,6-dimethyl-4,9-dioxo-8-pentyl-[1,5]-dioxonane-7-carboxylic acid isopropyl ester or Antimycin A3, and antimycin analogues disclosed in U.S. Pat. No. 7,241,804 (e.g., structures I-V); theaflavins; such as 3,4,6-trihydroxy-1-(3,5,7-trihydroxy-chroman-2-yl)-benzo-cyclohepten-5-one; epigallechatechins (EGCGs), such as 3,4,5-Trihydroxy-benzoic acid 5,7-dihydroxy-2-(3,4,5-tri-hydroxy-phenyl)-chroman-3-yl ester; benzenesulfonamides, such as ABT-737 or N-[4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide (a synthetic small-molecule inhibitor produced by NMR-guided, structure-based drug design (Abbott Laboratories, North Chicago, Ill.); indoles, such as GX15-070 (Gemin X, Montreal, Canada) or 2-[5-(3,5-Dimethyl-1H-pyrrol-2-ylmethylene)-4-methoxy-5H-pyroll-2-yl]-1H-indole; dibenzodiazocines, such as 2,9-Dimethoxy-11,12-di-hydro-dibenzo[c,g][1,2]diazocine 5,6-dioxide; and terphenyl derivatives, such as a compound having the following formula:

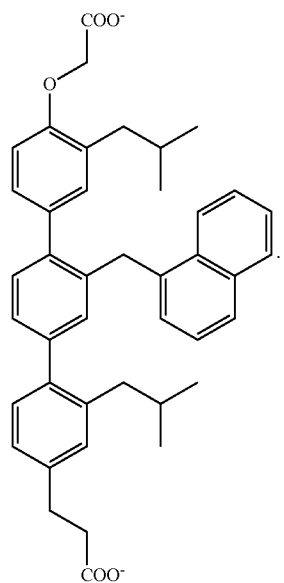

Side-by-side comparisons of these chemical inhibitors of antiapoptotic Bcl-2 proteins have not been reported, but their approximate rank-order potency with respect to affinity for the BH3 pocket of Bcl-2 or Bcl-$X_L$ appears to be ABT-737>EGCG>theafavins>gossypol>apogossypol>HA14-1 and antimycin. Accordingly, in one example the second agent administered to the cells is ABT-737 or N-[4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide.

The protease resistant Bcl-2/$IP_3R$ inhibiting polypeptide and/or amino acid sequence based treatment methods described herein may also be combined with any other methods generally employed in the treatment of the particular tumor, disease or disorder that the subject exhibits. So long as a particular therapeutic approach is not known to be detrimental to the patient's condition in itself, and does not significantly counteract the protease resistant Bcl-2/$IP_3R$ inhibiting polypeptide and/or amino acid sequence based treatment, its combination with the present invention is contemplated.

In another aspect, the protease resistant Bcl-2/$IP_3R$ inhibiting polypeptide and/or amino acid sequence can be co-administered with one or more anti-cellular agents. Examples anti-cellular agents include chemotherapeutic agents, as well as cytotoxins. Chemotherapeutic agents that can be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments can include agents such as cytokines. Basically, any anti-cellular agent may be used.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Examples of tumor suppressor agents are disclosed in U.S. Pat. Nos. 5,747,469; 5,677,178; and 5,756,455; 5,750,400; 5,654,155; 5,710,001; 5,756,294; 5,709, 999; 5,693,473; 5,753,441; 5,622,829; and 5,747,282 (each incorporated herein by reference), Other compositions that may be administered with the protease resistant Bcl-2/IP$_3$R inhibiting polypeptide and/or amino acid sequence, include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis It will be appreciated that the therapeutic agents administered with the protease resistant Bcl-2/IP$_3$R inhibiting polypeptide and/or amino acid sequence are not limited to the therapeutic agents described above, and that other therapeutic agents and other agents, which do not have therapeutic properties, can be used.

The following example is included to demonstrate different embodiments of the invention. It should be appreciated by those of skill in the art that the techniques disclosed in the example, which follow represent techniques discovered by the inventors to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

EXAMPLE

A synthetic IP$_3$R-derived peptide (IDP) is described in U.S. patent application Ser. No. 12/190,979, which is incorporated by reference in its entirety. The IDP corresponds to a 20 amino acid sequence within the Bcl-2-binding site on the IP$_3$R and functions as a competitive inhibitor of Bcl-2-IP$_3$R interaction. By disrupting this interaction IDP reverses Bcl-2-mediated inhibition of both IP$_3$-dependent channel opening and IP$_3$-dependent ER Ca$^{2+}$ release. Thus, when delivered into Bcl-2-positive T cells by fusion with the cell-penetrating peptide of HIV TAT (TAT-IDP) or by interaction with Chariot peptide uptake reagent, the IDP reverses Bcl-2-mediated inhibition of IP$_3$-dependent Ca$^{2+}$ elevation and apoptosis induced by anti-CD3 antibody.

Figure 17:
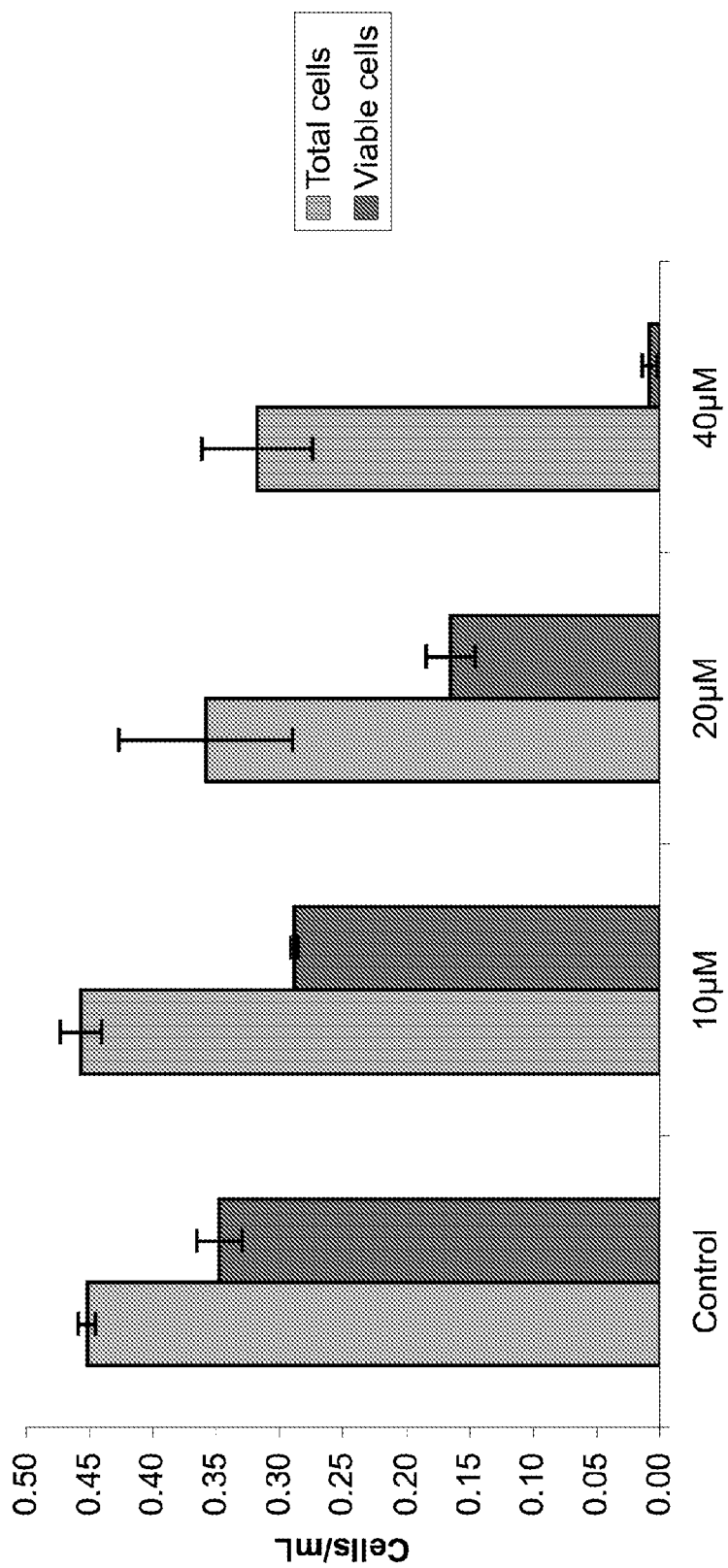
FIG. 17 illustrates a chart showing that TAT-IDP$_{DD/AA}$ (TAT-Pep8) kills multiple myeloma cells.

This Example describes the development of a TAT-IDP analogue, TAT-IDP$_{DD/AA}$, which induces striking Ca$^{2+}$ elevation in primary Chronic lymphocytic leukemia (CLL) cells by binding to the BH4 domain of Bcl-2 and disrupting Bcl-2-IP$_3$R interaction, thereby triggering Ca$^{2+}$-dependent apoptosis. These findings describe a novel approach to targeting Bcl-2 for therapeutic purposes. Also, the discovery that disrupting Bcl-2-IP$_3$R interaction is sufficient to induce IP$_3$R-mediated Ca$^{2+}$ elevation shows that Bcl-2 contributes to the pathophysiology of CLL by suppressing proapoptotic Ca$^{2+}$ signals downstream of constitutively active B cell receptor signals. Moreover, as shown in FIG. 17, TAT-IDP$_{DD/AA}$ disrupts Bcl-2-IP$_3$R interaction in multiple myelonoma cells, thereby apoptosis Materials and Methods Reagents Fura-2 AM and Hoechst 33342 were from Invitrogen. IDP and its analogues were synthesized by Genscript and were >95% pure by mass spectrometry and HPLC. BH4-Bcl-2 peptide was synthesized by Thermo Fisher at >80% purity. ABT-737 was provided by Stephen Tahir, Abbott Laboratories.

Cell Culture

WEHI7.2 cells were cultured in DMEM supplemented with 10% fetal calf serum, L-glutamine (2 mM), and nonessential amino acids (100 μM). Transfections of WEHI7.2 cells with expression vectors encoding wild type Bcl-2 and Bcl-2RS/GG were described previously. Jurkat cells and RS11846 cells were cultured in RPMI medium supplemented with 10% fetal bovine serum, L-glutamine (2 mM), and nonessential amino acids (100 μM). Cells were maintained in 5% carbon dioxide at high humidity.

CLL Cells and Normal Lymphocytes

Lymphocytes were freshly separated from heparinized peripheral blood obtained from normal adult volunteers or adult patients with chronic lymphocytic leukemia (CLL) meeting standard diagnostic guidelines. Patients had either never received treatment or had received treatment over two years prior to obtaining samples. We conformed to all guidelines and regulations in accordance with Internal Review Board protocols ICC2902/11-02-28 (Case Western Reserve University Cancer Center/University Hospitals of Cleveland Ireland Cancer Center). Cells were separated by centrifugation through Ficoll-Hypaque and suspended in RPMI medium supplemented with 10% fetal bovine serum, L-glutamine (2 mM), and nonessential amino acids (100 μM) at a density of 2 million cells/ml. Normal CD19+ B cells were pooled from healthy individuals between 26 and 32 years of age, in accordance with IRB-approval (as above). Mononuclear cells were separated by Ficoll-Hypaque centrifugation, and further isolation of B and T cells was achieved by magnetic separation using CD19 microbeads (Miltenyi Biotec, Bergisch Gladbach, Germany).

Digital Imaging of Intracellular Ca$^{2+}$

Methods of Ca$^{2+}$ imaging, described in detail previously, were employed here with only minor modification. Briefly, cells adhered to poly-L-lysine-coated coverslips (35-mm coverslip dishes, MatTek Corp., Ashland, Mass.) were loaded with 1 μM Fura-2 AM for 45 min at 25° C. in extracellular buffer (ECB) (130 mM NaCl, 5 mM KCl, 1.5 mM CaCl$_2$, 1 mM MgCl$_2$, 25 mM Hepes, pH 7.5, 1 mg/ml BSA, and 5 mM glucose). The buffer was replaced with fresh ECB and the incubation continued for 45 mM at 25° C. to permit de-esterification. Culture dishes were mounted on the non-heated stage of an inverted microscope (Olympus CKX41) equipped with a 20× Fluor objective. Excitation light was alternated between 340 and 380 nm by a filter wheel (Sutter Instrument Co.), with 0.8 sec and 0.2 sec exposure times respectively, and emitted light was filtered at >510 nm and collected with an intensified charge-coupled device camera (Cooke 12 bit VGA). The video signal was digitized using InCyt Im2 software (Intracellular Imaging) and subsequently processed using Microsoft Excel. To determine R$_{min}$ cells were perfused with ECB deficient in Ca$^{2+}$ and supplemented with 4 mM EGTA and 10 μM ionomycin. R$_{max}$ was obtained by perfusing cells with ECB supplemented with 4 mM CaCl$_2$ and 10 μM ionomycin. Ca$^{2+}$ concentration was calculated, based on the published K$_d$ for Fura-2 of 220 nM, by the equation of Grynkiewicz et al. Peptides were gently added to buffer overlaying the coverslip during continuous recording so as not disturb cells loosely adherent to the coverslip. In most experiments peptides were fused with the cell penetrating peptide of HIV TAT to facilitate uptake by cells. In some experiments peptides, without linkage to TAT, were delivered into cells using Chariot reagent (Active Motif) as previously described. Xestospongin C (Enzo Life Sciences International) and U73122 (Sigma), both dissolved in DMSO, were added to cells 30 mM prior to $Ca^{2+}$ measurements.

Comparison of Bcl-2 Levels by Western Blotting

Whole cell lysates were obtained by suspending cell pellets in cold SDS sample buffer. All samples were subjected to the Bradford assay in which total protein was quantified by obtaining a standard curve using known concentrations of bovine serum albumin. The absorbance of each lysate was measured at 595 nm in triplicate. Equal concentrations of protein were then loaded onto an SDS gel, transferred to a PVDF membrane, blocked in milk or bovine serum albumin solution, incubated with primary and secondary antibodies, and visualized by chemiluminescence. β-actin was used as a loading control. The following antibodies were employed: anti-human Bcl-2 (BD Biosciences, 551052); anti3 mouse/human Bcl-2 (Santa Cruz Biotechnology, sc7382); and anti-actin (Sigma, A5441).

Preparation of GST-Fusion Proteins, GST-Pull Downs and Western-Blot Analysis

BL21(DE3) Escherichia coli cells were transformed with pGEX-6p2 constructs containing cDNAs of $IP_3R1$ Domain 3 (a.a. 923-1581) and Domain 3DD/AA, in which Asp1403Asp1404 residues were mutated to Ala. The expressed proteins were purified as previously described (4, 5). Equal amounts (30 μg) of GST fusion proteins or GST (control) were incubated in Interaction Buffer (50 mM Tris-HCl, 300 mM NaCl, 1 mm EDTA, 1% NP-40, 0.5% sodium deoxycholate, 0.5% BSA, and protease inhibitor cocktail, pH 7.0) with 200 μg of cleared lysate from COS-7 cells transiently expressing 3× FLAG-Bcl-2 and immobilized on glutathione-Sepharose 4B beads (GE Healthcare) via rotation in a headover-head rotator for 2 h at 4° C. The beads were washed four times with modified Interaction Buffer (150 mM NaCl instead of 300 mM NaCl, without BSA) and complexed GST-fusion proteins were eluted by incubating the beads with 40 μl LDS® (Invitrogen) for 3 min at 95° C. and collected after centrifuging at 500×g for 5 mM Eluates (10 μl) were subjected to NUPAGE 4-12% Bis-Tris gel electrophoresis using MES/SDS-running buffer, transferred to an Immobilon-P PVDF membrane (Millipore) and assayed via Western-blot analysis. 3× FLAG-tagged Bcl-2 was detected using a mouse monoclonal ANTI-FLAG® M2-Peroxidase (HRP) antibody (Sigma-Aldrich). Total protein content was visualized by GelCode blue (Pierce) staining of the blot after film development. Quantification was done with ImageJ software.

Surface Plasmon Resonance (SPR) Measurements

The binding of GST-Domain3, GST-Domain3DD/AA and parental GST (control) to the BH4 domain of Bcl2 was analyzed by SPR at 25° C. using a Biacore 2000 instrument. All fusion proteins were affinity purified and dialyzed against standard PBS buffer without extra $Ca^{2+}$ or $Mg^{2+}$ (PBS: 2.67 mM KCl, 1.47 mM $KH_2PO_4$, 137.93 mM NaCl, 8.06 mM $Na_2HPO_4^{-}$ $7H_2O$; GIBCO) using Slide-A-Lyzer with a cut-off of 3-kDa (Pierce) to minimize the buffer effect. After dialysis, the concentration of the purified GST-fusion proteins was determined using BCA Protein Assay Reagent (Pierce), and the quality and integrity was examined by SDS-PAGE and GelCode blue (Pierce) prior to SPR analysis. Equal amounts (200 ng or 58.2 pmol of biotinylated peptide) of >80% pure biotinylated BH4-Bcl2 peptide (Biotin-RTGYDNREIVMKYIHYKLSQRGYEW) (SEQ ID NO: 8) and BH4-Bcl2-scrambled peptide (Biotin-WYEKQRSLHGIMYYVIEDRNTKGYR) (SEQ ID NO:9) were immobilized on 2 different flow cells of a streptavidin-coated sensor chip (BR-1000-32; Biacore, Uppsala, Sweden) using PBS supplemented with 0.005% P20 at pH 7.0. Measurements with GST-fusion proteins as analyte were performed in PBS at a flow rate of 30 μl/min Different concentrations of the analyte were used in a random order to assess binding (injection volume 120 μl). Bound peptide was removed by injection of 5 μl regeneration buffer (25 mM NaOH, 0.002% SDS) at 10 μl/min Background signals were obtained from the reference flow cell, containing the BH4-Bcl2-scrambled peptide, and were subtracted to generate response curves using Biaevaluation 3.0 software. In the analysis, only the association phase of the binding curve was taken into account. Data from 2-3 different sensorgrams for each condition were fitted by non-linear regression analysis to a Hill-Langmuir binding isotherm using Origin 7.0 (Northampton, Mass.) software.

Unidirectional 45Ca2+-Flux Assay

Twelve-well clusters containing MEF cells were fixed on a thermostated plate at 30° C. on a mechanical shaker. The culture medium was aspirated, and the cells were permeabilized by incubating them for 10 min in a solution containing 120 mM KCl, 30 mM imidazole-HCl (pH 6.8), 2 mM $MgCl_2$, 1 mM ATP, 1 mM EGTA and 20 μg/ml saponin. The non-mitochondrial $Ca^{2+}$ stores were then loaded for 45 min in 120 mM KCl, 30 mM imidazole-HCl (pH 6.8), 5 mM $MgCl_2$, 5 mM ATP, 0.44 mM EGTA, 10 mM $NaN_3$ and 150 nM free $^{45}Ca^{2+}$ (28 μCi/ml). Then, 1 ml of efflux medium containing 120 mM KCl, 30 mM imidazole-HCl (pH 6.8) and 1 mM EGTA was added and replaced every 2 min $IP_3$ (3 μM) was added for 2 min after 10 min of efflux. BH4-Bcl2 peptide (40 μM), in the presence or not of $IDP_{DD/AA}$ peptide (40 μM), was added from 4 min before $IP_3$ to 2 min after $IP_3$. At the end of the experiment, all $45Ca^{2+}$ remaining in the stores was released by incubation with 1 ml of a 2% (w/v) sodium dodecyl sulfate solution for 30 min $Ca^{2+}$ release was plotted as fractional loss (%/2 min) as a function of time, as previously described.

Biotin-Streptavidin Pulldown Assay

WEHI7.2 cells overexpressing wild type Bcl-2 were washed twice with PBS and incubated on ice for 30 min in 400 ul CHAPS lysis buffer (50 mM Tris-HCL pH 7.5, 100 mM NaCL, 2 mM EDTA, 1% CHAPS, 50 mM NaF, 1 mM Na3VO4, protease inhibitor cocktail, PhosSTOP). Cell lysates were centrifuged for 15 min at 20,000 g at 4 C and the supernatant (protein concentration 5 mg/ml) was continuously rotated with 200 μM biotin-Scr or biotin-IDPDD/AA, or without peptide, at 4 C for 16 hr. Streptavidin Sepharose beads (40 μA) (Pierce Pull-Down Biotinylated Protein:Protein Interaction Kit, Thermo, Cat #21115) were washed three times with tris buffered saline (25 mM Tris.HCL, 0.15M NaCl, pH 7) and then added to 400 μl cell lysate, followed by rotation for 2 hours at 4 C. After this, the beads were washed four times with tris buffered saline, centrifuging for 30-60 second each time. The beads were then incubated for 3-5 min at room temperature with 50 μl elution buffer provided with the Pierce pulldown kit (above) and centrifuged at 1,250×g for 30-60 seconds. The supernatant was boiled in SDS-PAGE sample buffer for 5 min and western blotting for Bcl-2 was performed as described above.

Co-Immunoprecipitation Assay

One hundred million WEHI7.2 cells overexpressing wild type Bcl-2 were washed twice with PBS and then lysed on ice for 30 min in 1 ml CHAPS buffer. The supernatant was prepared by centrifugation for 15 min at 20,000 g at 4° C. The supernatant (1 ml) was mixed with 100 μl 50% protein G in Tris 50 mM pH 7.5 buffer and rotated at 4 C for 2 hrs. After removing the beads, the supernatant was incubated with 200 μM peptide (Scr or IDPDD/AA, or without peptide addition, for 2 hrs at 4° C. Then hamster anti-human Bcl-2 antibody was added (final dilution 1:250) and the supernatant was rotated for 16 hrs at 4 C, followed by rotation in the presence of 50 μl protein G (50% beads) for 2 hours at 4 C. The beads were washed six times with CHAPS buffer and boiled for 5 min in SDS sample buffer followed by resolution of proteins by SDS-PAGE and analysis by western blotting for the IP$_3$R using anti-IP$_3$R antibody (BD Biosciences (Cat #610313) at 1:2,000 dilution and for Bcl-2 as described above.

Apoptosis Assays

Apoptosis was quantified according to apoptotic nuclear morphology and by detection of phosphatidylserine exposure on the plasma membrane. Apoptotic nuclear morphology was assessed by staining cells with Hoechst 33342 (10 mg/ml) for 15 min. Cells were visualized by epifluorescence microscopy (Zeiss Axiovert S100) using a 63× fluorescent oil objective (Carl Zeiss AG, Oberkochen, Germany) at excitation and emission wavelengths of 485 and 535 nm, respectively. Images were obtained using a chargecoupled device camera (Hamamatsu Photonics, Shizuoka, Japan) and digitally converted by Simple PCI software (Hamamatsu Photonics). Membrane translocation of phosphatidylserine was detected by Annexin V staining. Annexin V-positive cells were assessed by flow cytometry using an ARIA flow cytometer (Beckman Coulter, Pasadena, Calif., USA). All flow cytometry data were analyzed using FlowJo 8.8.4 for Macintosh (Treestar, Ashland, Oreg., USA). Dead cells were identified according to their inability to exclude trypan blue dye or propidium iodide. Trypan blue dye uptake into cells was detected by light microscopy using a 40× objective and quantified by counting up to 400 cells. Propidium iodide uptake was quantified by flow cytometry in association with the Annexin V measurement described above.

TAT-IDP Alone Induces Ca2+ Oscillations in Bcl-2-Expressing Lymphoma Cell Lines

Figure 2:
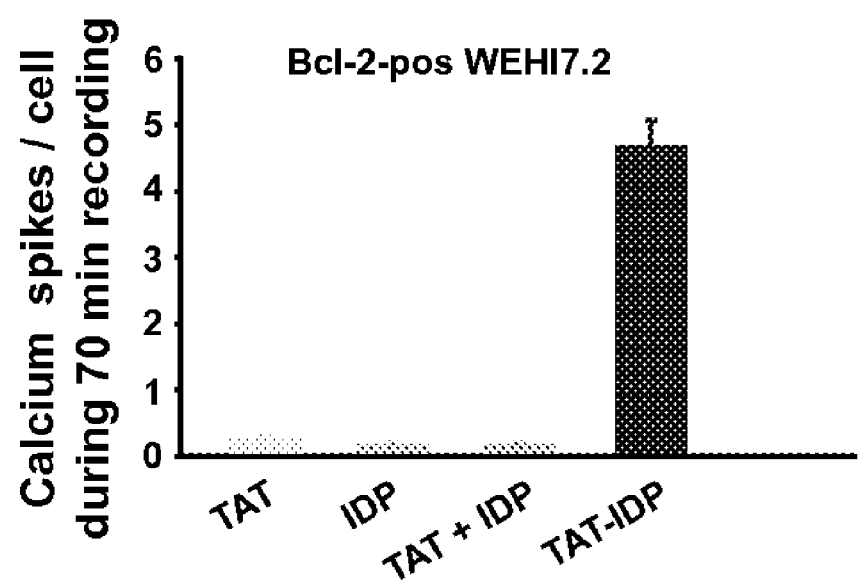
FIG. 2 illustrates a chart showing the number of $Ca^{2+}$ spikes observed per cell in 70 min recordings after adding 2 μM of the peptides shown (mean±SE, 67 cells total).

Four cell lines, representing lymphoid malignancies of both T cell and B cell origin, were employed to lay the foundation for studies using primary CLL cells. The sequence of TAT-IDP and its scrambled control analogue, TAT-Scr, are shown in FIG. 1, together with a diagram pinpointing the IP$_3$R region from which the IDP sequence was derived. Bcl-2 is virtually undetectable in the WEHI7.2 murine T cell lymphoma line and that Bcl-2 levels are similar in WEHI7.2 cells expressing wild type Bcl-2 or mutant Bcl-2$_{RS/GG}$, in which arginine 6 and serine 7 are both converted to glycine. We demonstrated previously that wild type Bcl-2 interacts with the IP$_3$R in these cells, whereas the Bcl-2$_{RS/GG}$ does not. In experiments summarized in FIG. 2, an average 6 Ca$^{2+}$ spikes per cell were observed when Bcl-2-positive WEHI7.2 cells were treated with TAT-IDP, whereas Ca$^{2+}$ spikes were very infrequent following treatment with TAT alone, IDP alone or a mixture of TAT and IDP. IDP also induced Ca$^{2+}$ elevations when introduced into the same cells by means of Chariot peptide uptake reagent (data not shown).

Figure 3:
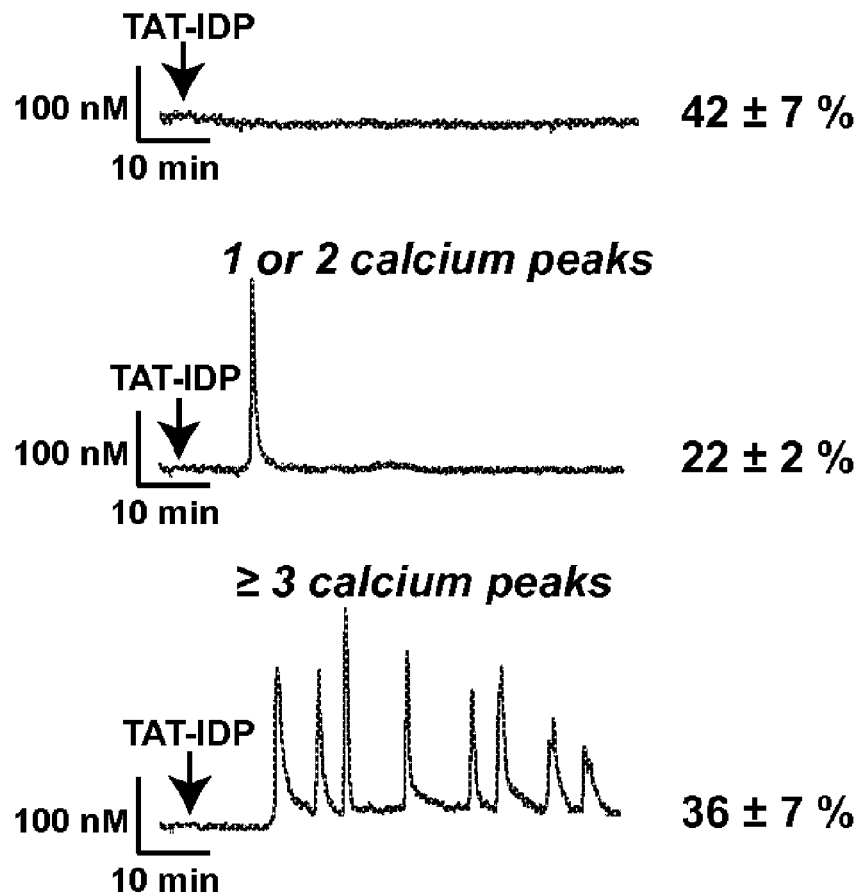
FIG. 3 illustrates charts showing representative single cell $Ca^{2+}$ recordings in Bcl-2-positive WEHI7.2 cells (2 μM TAT-IDP added at arrow); percentages (mean±SE) of cells displaying each pattern are based on 3 experiments (90 min recording, average 60 cells per recording).

The pattern of Ca$^{2+}$ elevation induced by TAT-IDP in Bcl-2-positive WEHI7.2 cells was analyzed by single cell digital imaging in a large number of experiments. As shown in FIG. 3, two patterns were arbitrarily defined. One or two isolated Ca$^{2+}$ oscillations were observed in 22±2% of cells; while a sustained pattern of Ca$^{2+}$ oscillations (three or more peaks) were observed in 36±7% of the cells. Thus, on average, over 50% of Bcl-2-positive cells reproducibly displayed Ca$^{2+}$ elevations in response to TATIDP. Notably, cell viability was not lost following TAT-IDP treatment (data not shown). Also, TAT-Scr did not induce Ca$^{2+}$ oscillations to a significant degree in Bcl-2-postive cells. Moreover, TAT-IDP did not induce Ca$^{2+}$ oscillations to nearly the same degree in Bcl-2-negative cells or in Bcl-2$_{RS/GG}$-positive cells as in cells expressing wild type Bcl-2.

In summary, these findings indicate that the IDP induces Ca$^{2+}$ oscillations when introduced into cells either by fusion with the cell penetrating peptide TAT or with a commercial peptide uptake reagent, and that this process is dependent upon Bcl-2.

TAT-IDPDD/AA is a More Effective Inducer of Ca$^{2+}$ Oscillations than TAT-IDP

Figure 4:
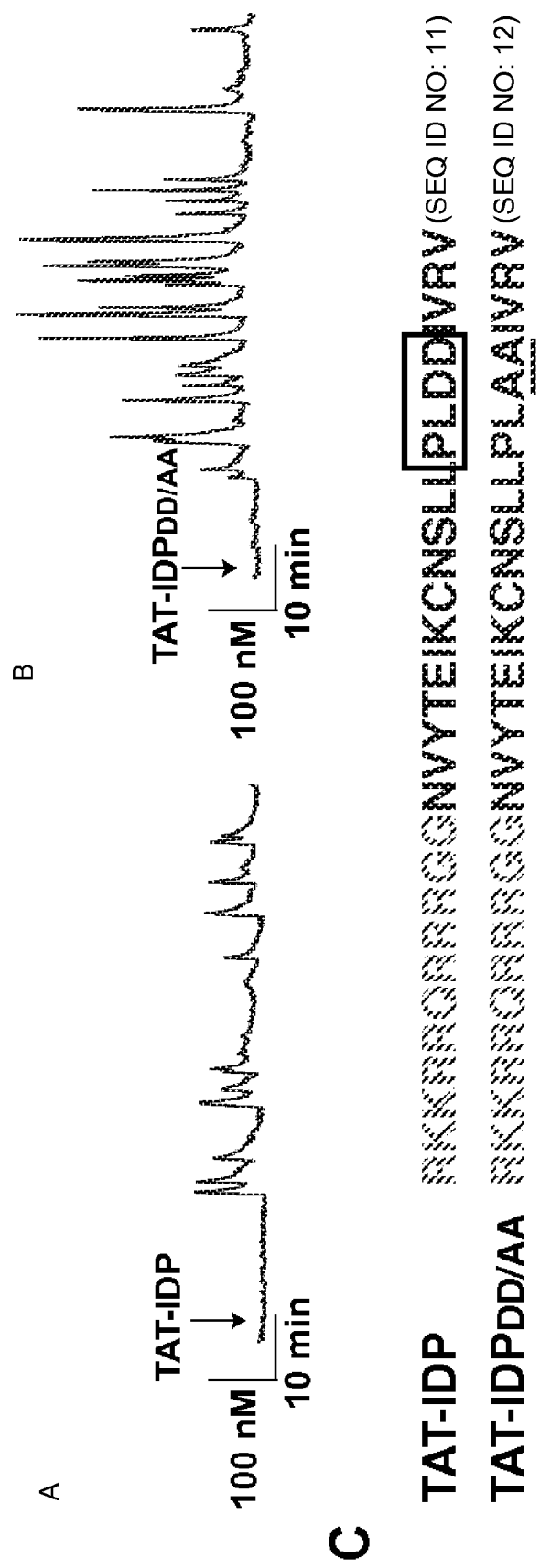
FIG. 4 illustrates charts showing single cell $Ca^{2+}$ recordings showing representative examples of $Ca^{2+}$ oscillations induced by 10 μM TAT-IDP or TATIDP$_{DD/AA}$ in over 50% of Jurkat cells (arrow, peptide addition) and peptide sequences showing the predicted aspartyl protease cleavage site in TAT-IDP (SEQ ID NO:) and its elimination by the DD/AA substitution in TAT-IDP$_{DD/AA}$ (SEQ ID NO: 12).

FIG. 4(A) shows TAT-IDP also induces Ca$^{2+}$ oscillations in the Jurkat human T cell leukemia line, which natively expresses Bcl-2 and in which we have previously documented interaction of endogenous Bcl-2 with the IP$_3$R. TAT-linked peptides are delivered into cells by macropinocytosis and are thus exposed to endocytic proteases, mainly cathepsins. Moreover, the presence of an aspartyl protease cleavage site, PLDD, in IDP was predicted by two algorithms (CLC Main Workbench and the CASVM server). The possibility that TAT-IDP may be subject to degradation when delivered into Jurkat cells was also suggested by a slight, but not significant, increase in both the percentage of cells displaying peptide-induced calcium elevations and a significant enhancement of the amplitude of these Ca$^{2+}$ elevations following pretreatment with the aspartyl protease inhibitor pepstatin A.

Figure 5:
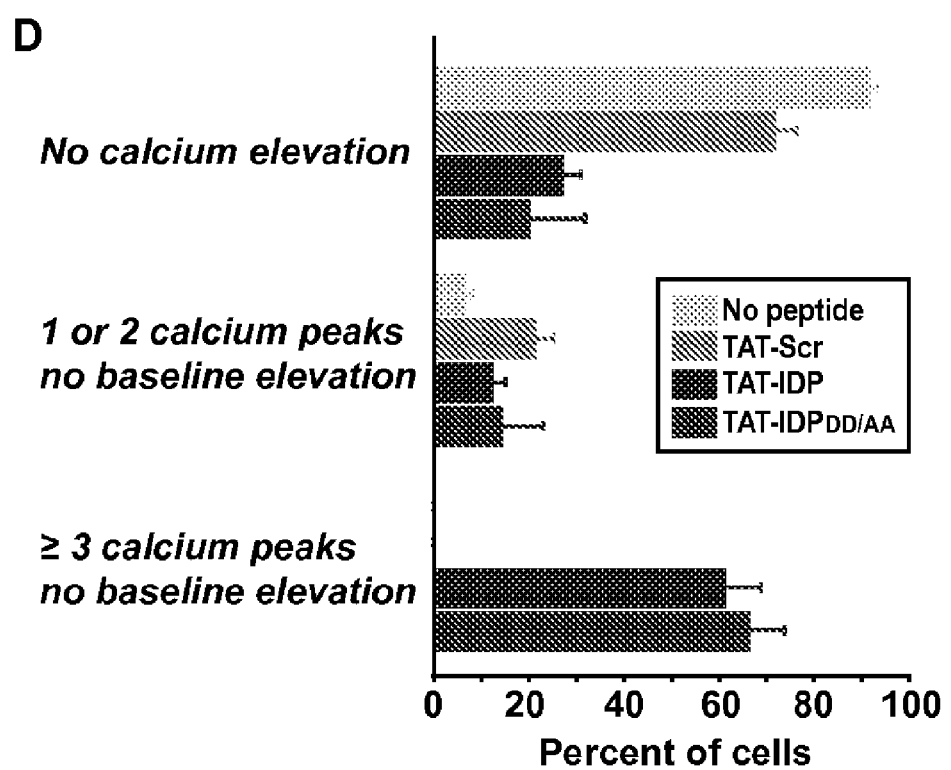
FIG. 5 illustrates a chart showing a percentage of Jurkat cells displaying each of three $Ca^{2+}$ response patterns when untreated or when treated with 10 μM TAT-Scr, TAT-IDP or TAT-IDP$_{DD/AA}$ (mean±SE, 6 experiments, average of 80 cells analyzed by 90 min single cell digital imaging per peptide treatment per experiment).

FIG. 4(C) shows an IDP analogue, TAT-IDP$_{DD/AA}$ that was generated with the goal of eliminating the predicted protease cleavage site. Representative Ca$^{2+}$ oscillations induced by TAT-IDP$_{DD/AA}$ are shown in FIG. 4(B). FIG. 5 shows TAT-IDP and TAT-IDP$_{DD/AA}$ induced Ca$^{2+}$ oscillations in a similar percentage of cells, but both the amplitude and frequency of Ca$^{2+}$ oscillations were much higher with TAT-IDP$_{DD/AA}$ than with TAT-IDP. Another peptide analogue, in which the predicted protease cleavage site is eliminated without altering overall peptide charge, TATIDP$_{DD/EE}$, also induced Ca$^{2+}$ oscillations of higher amplitude and frequency, very similar to TAT-IDP$_{DD/AA}$.

Figure 6:
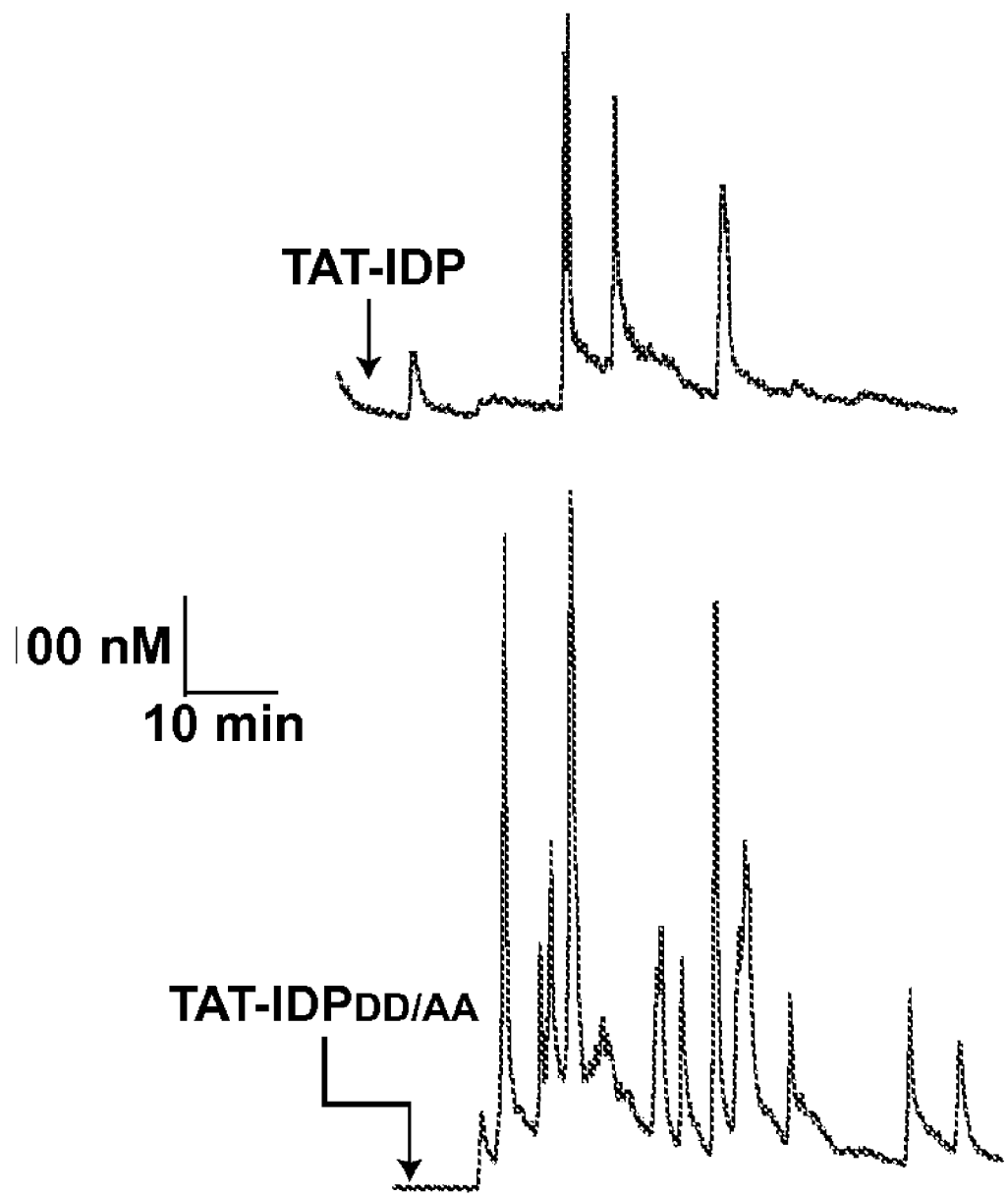
FIG. 6 illustrates a charts of a single cell $Ca^{2+}$ recordings showing representative examples of $Ca^{2+}$ oscillations induced by 10 μM TAT-IDP or TAT-IDP$_{DD/AA}$ in over 50% of RS11846 cells (arrow, peptide addition).

Also, the increased activity of TAT-IDP$_{DD/AA}$ compared to TAT-IDP was observed in the RS11846 human B cell lymphoma line, which has elevated Bcl-2due to a t(14;18) chromosomal translocation typical of human follicular lymphoma (FIG. 6). Thus, the induction of Ca$^{2+}$ oscillations by these peptides is not unique to T lymphocytes.

Figure 7:
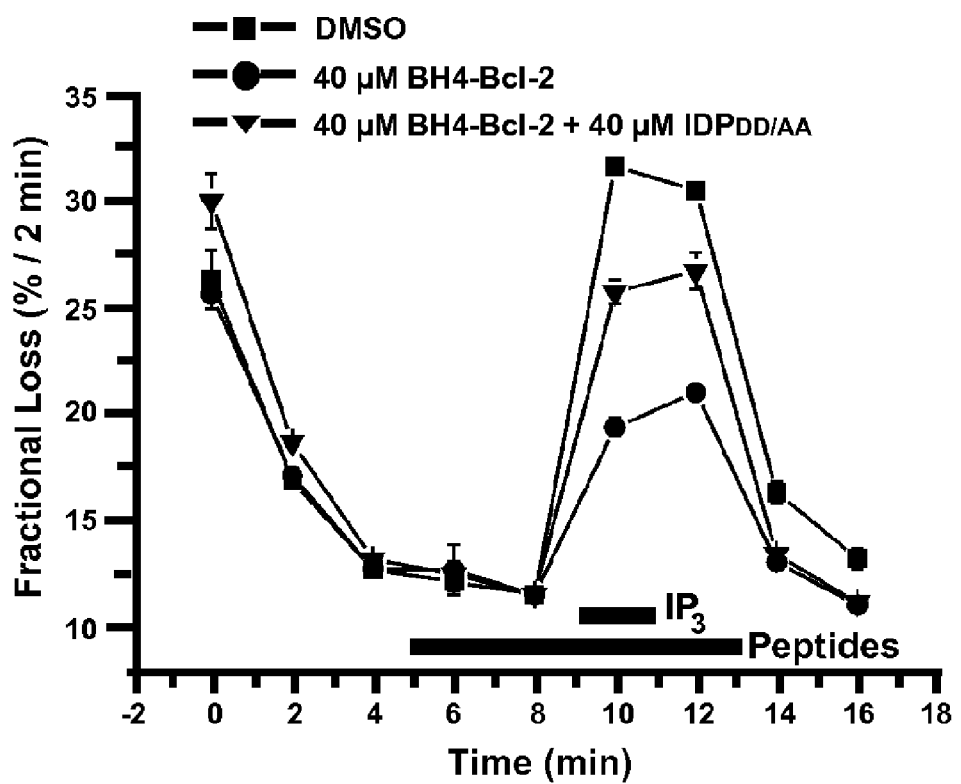
FIG. 7 illustrates a chart showing IDP$_{DD/AA}$ prevents the inhibition of $IP_3R$-mediated $Ca^{2+}$ release by BH4-Bcl-2, a peptide corresponding to the BH4 domain Bcl-2. A typical unidirectional $45Ca^{2+}$-efflux experiment showing the $Ca^{2+}$ release induced by 3 μM $IP_3$ from permeabilized $45Ca^{2+}$-loaded wild-type MEF cells in the presence of vehicle (filled squares), 40 μM BH4-Bcl-2 peptide (filled circles), 40 μM BH4-Bcl-2 peptide and 40 μM IDP$_{DD/AA}$ (filled triangles). All peptides were incubated from 4 min before the addition of $IP_3$ to 2 min after its addition (bars). Data points of a representative experiment, plotted as fractional loss (%/2 min) as a function of time, were obtained in duplicate and represent mean±SD.

TAT-IDP$_{DD/AA}$ Binds to the BH4 Domain of Bcl-2 to Disrupt Bcl-2-IP$_3$R Interaction and Induce Ca2+ Oscillations Since TAT-IDP$_{DD/AA}$ was significantly more effective at inducing Ca$^{2+}$ oscillations than TAT-IDP, we investigated its mechanism of action at a biochemical level. GST-pull down experiments showed that, binding of 3xFLAG-Bcl-2 to GST-Domain3 was not significantly different from the binding to GST-Domain3DD/AA. Furthermore, the binding of these GST-tagged domains to the Biotin-BH4-Bcl-2 (i.e., a biotin-tagged peptide corresponding to the BH4 domain of Bcl-2) was measured by surface plasmon resonance. The results indicate GST-Domain3 and GST-Domain3DD/AA bind specifically to Biotin-BH4-Bcl-2 with similar affinities. Also, interaction of IDP$_{DD/AA}$ with Bcl-2was documented by biotin-streptavidin pull down and disruption of Bcl-2-IP$_3$R interaction by IDP$_{DD/AA}$ was confirmed in co-immunoprecipitation experiments. Consistent with these observations, FIG. 7 shows IDP$_{DD/AA}$ reversed the Bcl-2-imposed inhibition of IP$_3$-induced $^{45}$Ca$^{2+}$ efflux from the ER when added to cells after $^{45}$Ca$^{2+}$ loading and permeabilization with digitonin, as shown previously for IDP.

Finally, the IP$_3$R inhibitor xestospongin C and the phospholipase C inhibitor U73122 reduced the percentage of cells displaying peptide-induced Ca$^{2+}$ oscillations, providing further evidence that Ca$^{2+}$ responses to both TAT-IDP and TAT-IDP$_{DD/AA}$ were IP$_3$R-dependent (FIG. 8A). Also, each of these peptides induced Ca$^{2+}$ oscillations in DT40 cell B cell lymphoma line, which expresses all three IP$_3$R isoforms (FIG. 8B), but the induction of Ca$^{2+}$ oscillations by these peptides was significantly less in triple IP$_3$R knockout DT40 cells (FIG. 8C).

In summary, these findings show that the increase in Ca$^{2+}$ responses induced in Bcl-2-positive cell lines by TAT-IDP$_{DD/AA}$ compared to TAT-IDP is likely due to increased cellular uptake and stability as a result of reduced proteolytic cleavage rather than increased affinity of TAT-IDP$_{DD/AA}$ for Bcl-2. In addition, these findings confirm that TAT-IDP$_{DD/AA}$ functions as a competitive inhibitor of Bcl-2-IP$_3$R interaction, as shown previously for TAT-IDP.

TAT-IDPDD/AA Induces Striking Ca2+ Elevation in Primary CLL Cells

The effects of these peptides were next investigated in primary CLL cells, chosen for this purpose because CLL is invariably associated with an elevated level of Bcl-2 and because Bcl-2 plays an important role in apoptosis resistance in this disease. CLL cells were isolated from peripheral blood of untreated patients. Malignant lymphocytes, which represented over 80% of lymphocytes in peripheral blood samples, were separated by density gradient separation and used immediately in experiments without interval storage.

Figure 9:
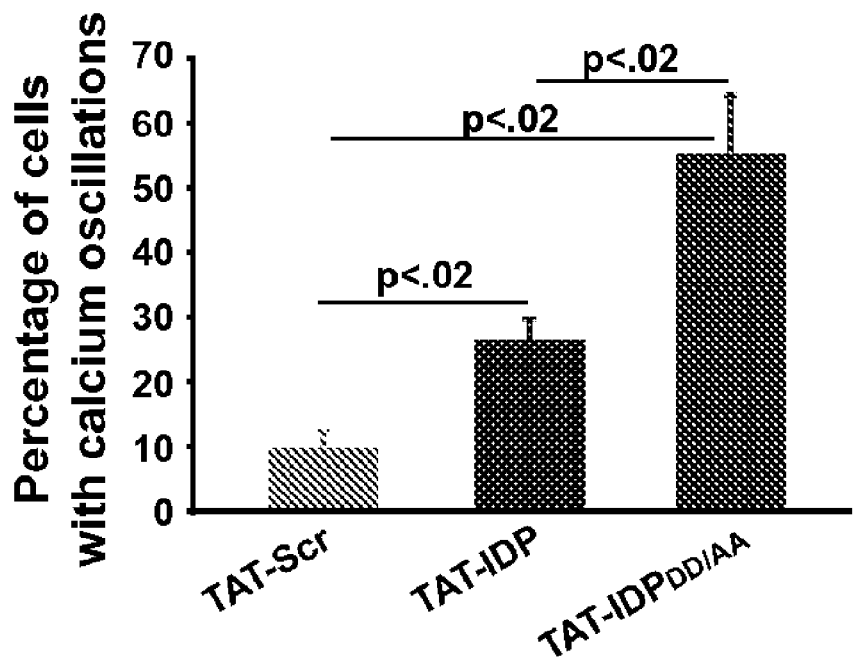
FIG. 9 illustrates a chart showing the percentage of CLL cells displaying $Ca^{2+}$ oscillations in response to 10 μM peptide addition during 90 min single cell recordings (mean±SE, 3 experiments each using CLL cells isolated from a different patient, average 85 cells per experiment).

The patterns of Ca$^{2+}$ elevation induced by TAT-Scr, TAT-IDP and TAT-IDP$_{DD/AA}$ in CLL cells are summarized quantitatively in FIG. 9. Less than 10% of untreated cells (not shown) or TAT-Scr-treated cells had detectable Ca$^{2+}$ elevations in recordings that were typically 90 min in duration. TAT-IDP induced Ca2+ elevation in only 26 ±2% of CLL cells, corresponding to either single or dual spikes (14 ±2%) or repetitive oscillations (≥3 successive Ca$^{2+}$ spikes) (12 ±2%). Thus, overall Ca$^{2+}$ responses to TAT-IDP were much less than observed in the cell lines investigated in this study. On the other hand, TAT-IDPDD/AA induced Ca$^{2+}$ elevation in 51 ±5% of CLL cells isolated from 7 patients.

The response patterns and percentages of responses were remarkably similar among the individual patient samples. Several different patterns of Ca$^{2+}$ elevation were observed in CLL cells following TATIDP$_{DD/AA}$ addition. One pattern, observed in only 6±2% of cells, consisted of prolonged Ca$^{2+}$ oscillations without baseline Ca$^{2+}$ elevation, similar to the patterns observed previously in Bcl-2-positive cell lines described above. The more prominent patterns included one or two high amplitude spikes associated with prolonged basal Ca$^{2+}$ elevation (28±5% of cells) or a relatively brief burst of Ca$^{2+}$ oscillations, also associated with prolonged basal Ca$^{2+}$ elevation (17±4% of cells).

Figure 10:
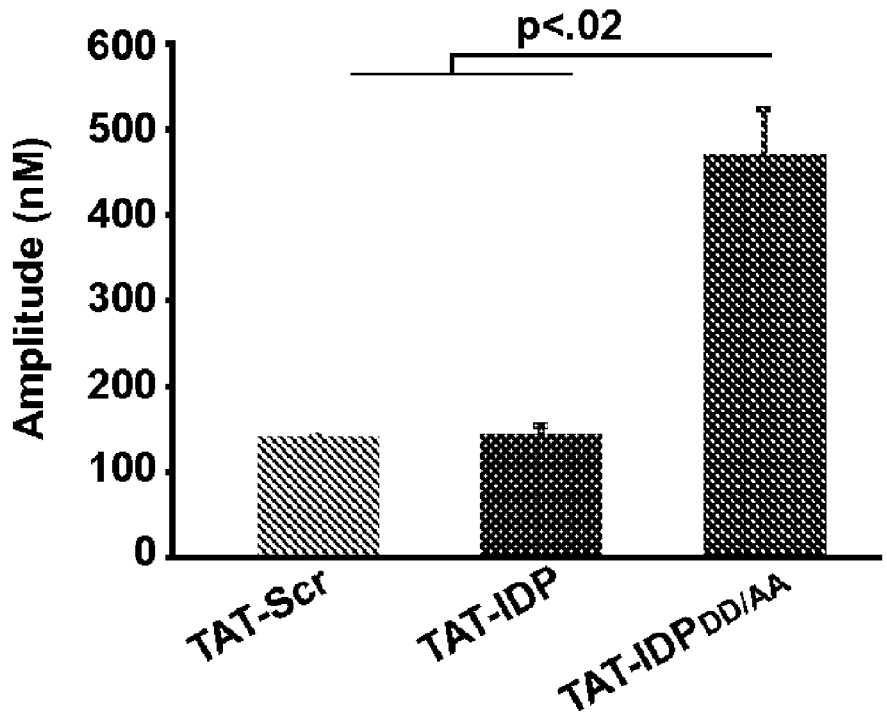
FIG. 10 illustrates a chart showing the amplitude of individual $Ca^{2+}$ spikes in the same experiments as in FIG. 9 (mean±SE).
Figure 12:
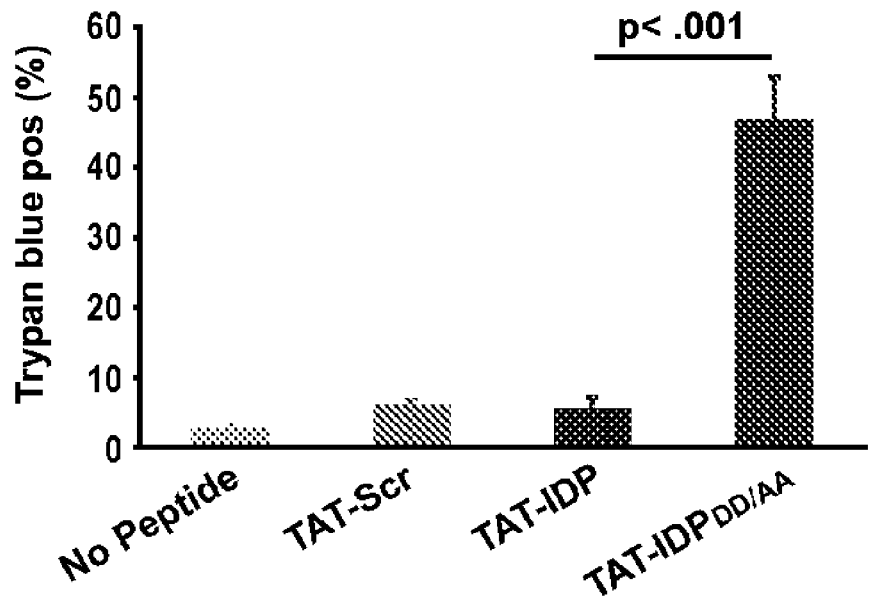
FIG. 12 illustrates a chart showing the results of CLL cells from 8 patients that were treated with 10 μM of each peptide shown and the percentage of dead cells, identified by trypan blue dye uptake, was determined 24 hr later; results are presented as mean±SE.
Figure 13:
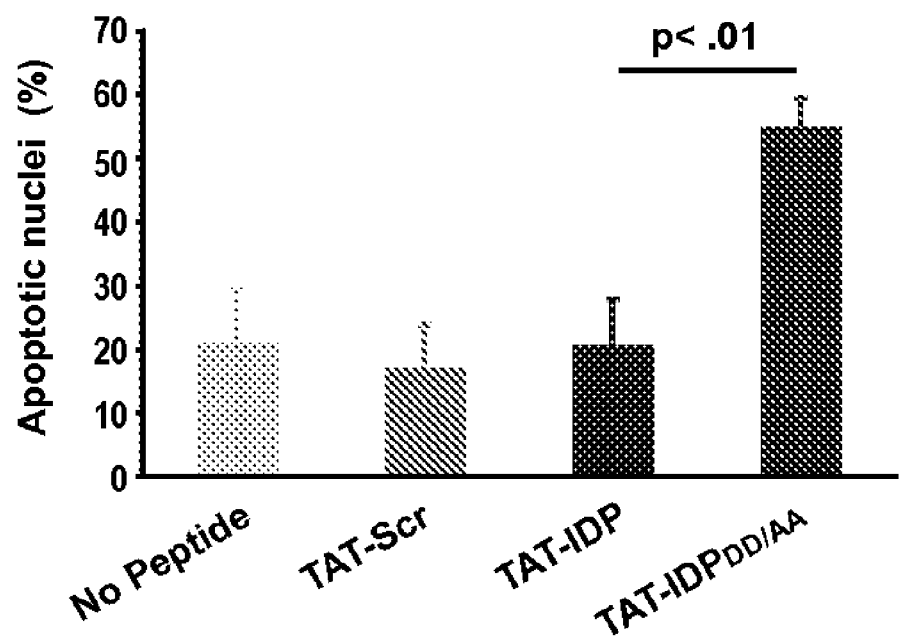
FIG. 13 illustrates a chart showing the results CLL cells from 4 different patients were treated with 10 μM of each peptide shown and 24 hr later the percentage of cells (mean±SE) with typical apoptotic morphology was determined by fluorescence microscopic analysis of Hoechst-stained nuclei.
Figure 14:
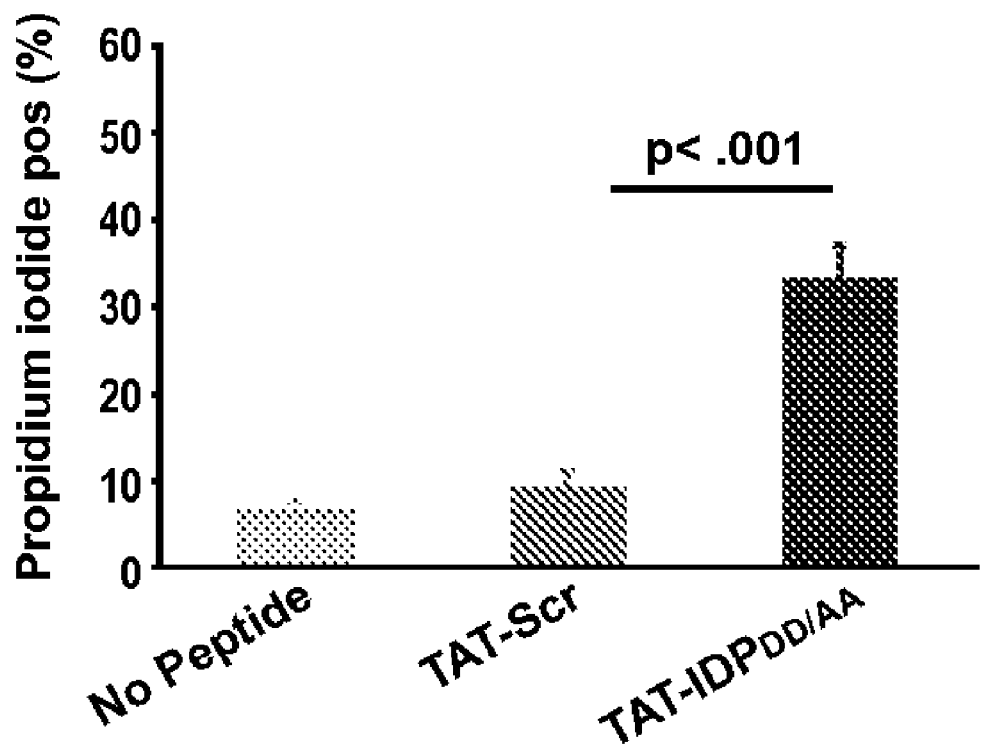
FIG. 14 illustrates a chart showing the results of experiments using CLL cells from 6 patients to quantify the percentage of dead cells (mean±SE) by flow cytometric analysis of propidium iodide uptake 24 hr after treatment with 10 μM of the peptides shown.

Analysis of multiple experiments monitoring Ca$^{2+}$ responses in a large number of cells documents that differences in the relatively abilities of TAT-Scr, TAT-IDP and TAT-IDP$_{DD/AA}$ to induce Ca$^{2+}$ elevations are highly significant. In addition, FIG. 10 shows the amplitude of Ca$^{2+}$ peaks was significantly higher following TAT-IDP$_{DD/AA}$ compared to TAT-IDP. While differing in pattern and amplitude, the Ca$^{2+}$ responses to both TAT-IDP (data not shown) and TAT-IDPDD/AA were inhibited by xestospongin C, consistent with a role for IP$_3$R-mediated Ca$^{2+}$ release in the initiation of Ca$^{2+}$ elevations by both peptides.

In contrast to peptide-induced Ca$^{2+}$ elevation, the BH3-mimetic ABT-737 did not induce Ca$^{2+}$ elevation in CLL cells, even though ABT-737 induced the death of 40% of CLL cells at 24 hr. This latter finding underscores the difference in mechanism between ABT-737 and peptides designed to inhibit Bcl-2 binding to the IP$_3$R.

In summary, the findings indicate that TAT-IDP$_{DD/AA}$ induces significant Ca$^{2+}$ elevation in primary CLL cells and that the pattern of Ca$^{2+}$ elevation is different from that elicited by TAT-IDP$_{DD/AA}$ in Bcl-2-positive cell lines. Two main differences were detected: first, TAT-IDP$_{DD/AA}$ induced only a brief period of Ca$^{2+}$ spiking rather than prolonged Ca$^{2+}$ oscillations; second, following TAT-IDP$_{DD/AA}$ addition, the brief period of Ca$^{2+}$ spiking in CLL cells was followed by a continuous cytoplasmic Ca$^{2+}$ elevation not observed in the cell lines.

Figure 15:
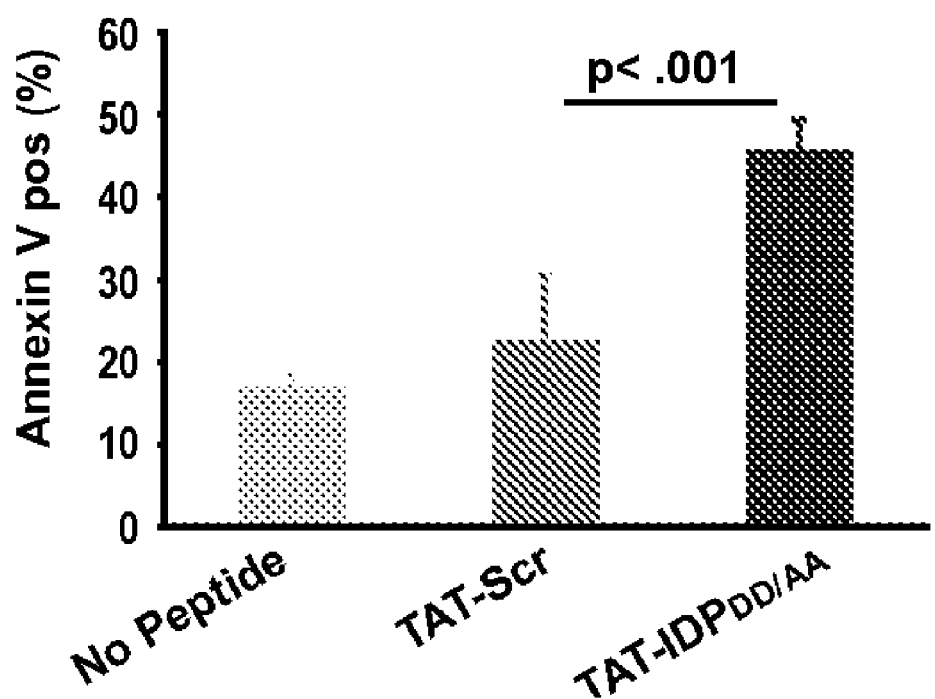
FIG. 15 illustrates a chart showing the results of flow cytometric analysis of the same samples as in FIG. 14, quantifying the percentage of Annexin V positive cells (mean±SE) 24 hr after treatment with 10 μM of the peptides shown.
Figure 16:
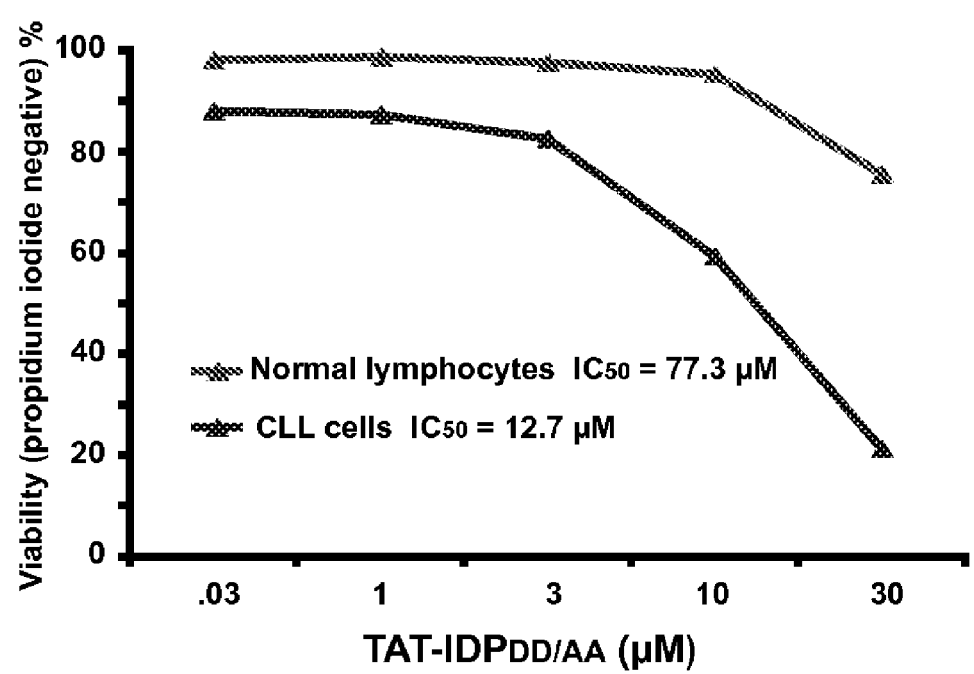
FIG. 16 illustrates dose-response curves comparing viability of CLL cells versus normal lymphocytes, based on flow cytometric quantification of propidium iodide exclusion 24 hr after adding 10 μM TAT-IDP$_{DD/AA}$. Results are representative of two side-by-side comparisons employing CLL cells and normal cells from different donors.

TAT-IDP$_{DD/AA}$-Evoked Ca$^{2+}$ Elevation Induces Apoptosis in Primary CLL Cells but not in Normal Lymphocytes Because continuous cytoplasmic Ca$^{2+}$ elevation can trigger apoptosis and necrosis, the effects of TATIDP$_{DD/AA}$ on CLL cell viability were tested. As shown in Figs. 12-15, TAT-IDP$_{DD/AA}$-mediated Ca$^{2+}$ elevation induced substantial apoptosis in CLL cells. This was observed consistently in CLL samples isolated from eight patients. Cell death was documented by trypan blue dye uptake (FIG. 12) and propidium iodide uptake (FIG. 14), while apoptosis induction was documented by observing apoptotic nuclear morphology (FIG. 13) and by detecting phosphatidylserine exposure on the cell surface with Annexin V (FIG. 15). The induction of cell death was specific to TAT-IDP$_{DD/AA}$, since neither TAT-Scr nor TAT-IDP induced apoptosis in CLL cells. Moreover, apoptosis induction by TAT-IDPDD/AA was inhibited by xestospongin C, confirming the role of IP$_3$R-mediated Ca$^{2+}$ elevation in this process. Importantly, CLL cells were over 6-fold more sensitive to apoptosis induction by TAT-IDP$_{DD/AA}$ than normal peripheral blood lymphocytes (FIG. 16), suggesting that TAT-IDP$_{DDIAA}$ may selectively target leukemia cells that overexpress Bcl-2.

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

Having described the invention, we claim the following:

1. A method of inducing apoptosis in a lymphoma, leukemia, or a multiple myeloma cell expressing Bcl-2 and IP$_3$R, comprising:
   administering to the lymphoma, leukemia, or multiple myeloma cell, wherein the cell overexpresses Bcl-2, a therapeutically effective amount of a polypeptide that inhibits binding of Bcl-2 to IP$_3$ receptors (IP$_3$R) of cells that express IP$_3$R and Bcl-2, the polypeptide comprising an amino acid sequence selected from the group consisting of SEQ ID NOs: 6, and 7, and a transport moiety that facilitates transport of the purified peptide across a biological membrane.

2. The method of claim 1, the polypeptide reversing the interaction of Bcl-2 with IP$_3$R of cells that express IP$_3$R and Bcl-2.

3. The method of claim 1, further comprising administering a second agent to the cells that inhibits binding of Bcl-2 to BH3 pro-apoptotic proteins.

4. The method of claim 3, the second agent comprising N-(4-(4-(4'-chloro-biphenyl-2-ylmethyl)-piperazin-1-yl)-bezoyl)-4-(3-dimethylamino-1-phenylsulfanylmethyl-propylamino)-3-nitro-benzenesulfonamide ABT-737.

5. A method of treating a neoplastic disorder in a subject, comprising:
  administering to neoplastic cells of the subject expressing IP$_3$R and Bcl-2, wherein the neoplastic cells overexpress Bcl-2, a therapeutically effective amount of a polypeptide that inhibits binding of Bcl-2 to IP$_3$ receptors (IP$_3$R) of cells that express IP$_3$R and Bcl-2, the polypeptide comprising an amino acid sequence selected from the group consisting of SEQ ID NOs: 6,and 7, and a transport moiety that facilitates transport of the purified peptide across a biological membrane:
  wherein the neoplastic disorder comprises lymphoma, leukemia, or multiple myeloma.

6. The method of claim 5, the polypeptide reversing the interaction of Bcl-2 with IP$_3$R of cells that express IP$_3$R and Bcl-2.

7. The method of claim 5, further comprising administering a second agent to the cells that inhibits binding of Bcl-2 to BH3 pro-apoptotic proteins.

8. The method of claim 7, the second agent comprising N-(4-(4-(4'-chloro-biphenyl-2-ylmethyl)-piperazin-1-yl)-bezoyl)-4-(3-dimethylamino-1-phenylsulfanylmethyl-propylamino)-3-nitro-benzenesulfonamide or ABT-737.

9. The method of claim 5, wherein the neoplastic disorder comprises chronic lymphocytic leukemia or multiple myeloma.

10. The method of claim 1, the polypeptide having an amino acid sequence comprising SEQ ID NO: 12.

11. The method of claim 5, the polypeptide having an amino acid sequence comprising SEQ ID NO: 12.

* * * * *

UNITED STATES PATENT AND TRADEMARK OFFICE
CERTIFICATE OF CORRECTION

PATENT NO. : 9,657,073 B2  
APPLICATION NO. : 13/819980  
DATED : May 23, 2017  
INVENTOR(S) : Clark Distelhorst et al.

Page 1 of 1

It is certified that error appears in the above-identified patent and that said Letters Patent is hereby corrected as shown below:

In the Specification

Column 1, Line 14 reads "085804" should read --CA085804--

Signed and Sealed this
Twenty-sixth Day of December, 2017

Joseph Matal
*Performing the Functions and Duties of the
Under Secretary of Commerce for Intellectual Property and
Director of the United States Patent and Trademark Office*